US008394835B2

(12) United States Patent
Aydt et al.

(10) Patent No.: US 8,394,835 B2
(45) Date of Patent: Mar. 12, 2013

(54) AROMATIC COMPOUNDS AND THEIR USE IN MEDICAL APPLICATIONS

(75) Inventors: Ewald Aydt, Berlin (DE); Remo Kranich, Berlin (DE); Anke Busemann, Henningsdorf (DE)

(73) Assignee: Revotar Biopharmaceuticals AG (DE)

( * ) Notice: Subject to any disclaimer, the term of this patent is extended or adjusted under 35 U.S.C. 154(b) by 0 days.

(21) Appl. No.: 13/037,575

(22) Filed: Mar. 1, 2011

(65) Prior Publication Data

US 2011/0152291 A1 Jun. 23, 2011

Related U.S. Application Data

(62) Division of application No. 12/067,389, filed as application No. PCT/EP2006/009154 on Sep. 20, 2006, now Pat. No. 7,923,473.

(30) Foreign Application Priority Data

Sep. 20, 2005 (EP) .................................... 05020510

(51) Int. Cl.
*A61K 31/44* (2006.01)
*C07D 421/00* (2006.01)
(52) U.S. Cl. ....................... 514/336; 546/268.1; 546/256
(58) Field of Classification Search .................. 514/336; 546/268.1, 256
See application file for complete search history.

(56) References Cited

U.S. PATENT DOCUMENTS

| 4,363,813 | A | 12/1982 | Kawasaki et al. |
| 4,476,219 | A | 10/1984 | Sakanoue et al. |
| 5,374,772 | A | 12/1994 | Carson et al. |
| 6,248,790 | B1 | 6/2001 | Uckun et al. |
| 6,340,700 | B1 | 1/2002 | Chabrier de Lassauniere et al. |
| 6,432,957 | B1 | 8/2002 | Kodoma et al. |
| 7,851,501 | B2 * | 12/2010 | Aydt et al. ..................... 514/438 |
| 7,919,532 | B2 | 4/2011 | Aydt et al. |
| 2003/0187306 | A1 | 10/2003 | Sinha et al. |
| 2005/0113416 | A1 | 5/2005 | Wang et al. |
| 2006/0100245 | A1 * | 5/2006 | Bakthavatchalam et al. . 514/332 |
| 2008/0249107 | A1 | 10/2008 | Kranich et al. |
| 2009/0030015 | A1 | 1/2009 | Kranich et al. |
| 2011/0053939 | A1 | 3/2011 | Aydt et al. |
| 2011/0142765 | A1 | 6/2011 | Aydt et al. |

FOREIGN PATENT DOCUMENTS

| EP | 0217204 A1 | 4/1987 |
| EP | 0465122 A1 | 1/1992 |
| EP | 0426468 B1 | 9/1995 |
| EP | 0840606 B1 | 6/2000 |
| EP | 1081151 | 3/2001 |
| EP | 0758243 B1 | 3/2003 |
| EP | 1481669 A1 | 12/2004 |
| EP | 1577289 A1 | 9/2005 |
| EP | 1627644 A1 | 2/2006 |
| JP | 10-306024 | 11/1998 |
| JP | 2003 055369 A | 6/2003 |
| WO | WO 97/01335 | 1/1997 |
| WO | WO 97/01569 A1 | 1/1997 |
| WO | WO 99/29705 A2 | 6/1999 |
| WO | WO 99/29705 A3 | 6/1999 |
| WO | WO 99/29706 A2 | 6/1999 |
| WO | WO 99/29706 A3 | 6/1999 |
| WO | WO 00/33836 A1 | 6/2000 |
| WO | WO 03/075905 A1 | 9/2003 |
| WO | WO 03/097658 A2 | 11/2003 |
| WO | WO 03/097658 A3 | 11/2003 |
| WO | 2004/018428 A1 | 3/2004 |
| WO | WO 2004/018502 A1 | 3/2004 |
| WO | 2004/054977 A1 | 7/2004 |
| WO | 2005/046683 A1 | 5/2005 |
| WO | WO 2005/090284 A1 | 9/2005 |
| WO | WO 2007/039111 A3 | 4/2007 |
| WO | WO 2007/039112 A1 | 4/2007 |
| WO | WO 2007/039113 A1 | 4/2007 |
| WO | WO 2007/039114 A1 | 4/2007 |

OTHER PUBLICATIONS

Bakthavatchalam et al. CAS: 141: 89019, 2004.*
Badcock et al., "The Chemistry of the 'Insoluble Red' Woods. Part IV. Some Mixed Benzoins," J. Chem. Soc. 2961-2965 (1950).
Whalley, "The Isomerization of isoFlavones," J. Chem. Soc. 3366-3371 (1953).
Feb. 17, 2012, Office Action in U.S. Appl. No. 13/032,760.
Mar. 8, 2012, Office Action in U.S. Appl. No. 10/593,259.
R.P. McEver, "8 Interactions of Selectins with PSGL-I and Other Ligands," Ernst Schering Res. Found. Workshop 44:137-147 (2004).
G. Constantin, "PSGL-I as a Novel Therapeutic Target," Drug News Perspect 17(9):579-586 (Nov. 2004).
Okazaki et al., "Enhancement of Metastatic Activity of Colon Cancer as influenced by Expression of Cell Surface Antigens," Journal of Surgical Research 78(JR985298):78-84 (Sep. 22, 1997).
A.M. Müller et al., "Heterogeneous expression of cell adhesion molecules by endothelial cells in ARDS," Journal of Pathology 198(2):270-275 (2002).
R.P. McEver, "Selectin-carbohydrate interactions during inflammation and metastasis," Glycoconjugate Journal 14:585-591 (1997).
R.P. McEver et al., "Perspectives Series: Cell Adhesion in Vascular Biology" "Role of PSGL-I Binding to Selectins in Leukocyte Recruitment," J. Clin. Invest., The American Society for Clinical Investigation, Inc. 100(3):485-492 (Aug. 1997).
A. Di Stefano et al., "Upregulation of Adhesion Molecules in the Bronchial Mucosa of Subjects with Chronic Obstructive Bronchitis," Am. J. Respir. Crit. Care. Med. 149(3):803-810 (1994).
S. Terajima et al., "An important role of tumor necrosis factor-α in the induction of adhesion molecules in psoriasis," Arch. Dermatol. Res. 290:246-252 (1998).
M. Sperandio et al., "Blocking Leukocyte Rolling: Does it have a Role in Disease Prevention?" Vascular Disease Prevention 1:185-195 (2004).

(Continued)

*Primary Examiner* — Rei-tsang Shiao
(74) *Attorney, Agent, or Firm* — J.A. Lindeman & Co., PLLC

(57) ABSTRACT

Pharmaceutical compositions comprising at least one compound of the formulas (Ia) or (Ib) and a pharmaceutically acceptable carrier wherein the symbols have the following meaning —X— is e.g. and Y being e.g. or the pharmaceutically acceptable salts can be applied to modulate the in-vitro and in-vivo binding processes mediated by E-, P- or L-selectin binding.

16 Claims, No Drawings

OTHER PUBLICATIONS

C.A. Lipinski et al., "Experimental and computational approaches to estimate solubility and permeability in drug discovery and development settings," Advanced Drug Delivery Reviews, 23:3-25 (1997).

H. Ulbrich et al., "Leukocyte and endothelial cell adhesion molecules as targets for therapeutic interventions in inflammatory disease," Trends in Pharmacological Sciences 24(12):640-647 (2003).

S.J. Romano, "Selectin Antagonists, Therapeutic Potential in Asthma and COPD," Treat. Respir. Med. 4(2):85-94 (2005).

M.P. Schön, "Inhibitors of selectin functions in the treatment of inflammatory skin disorders," Therapeutics and Clinical Risk Management 1(3):201-208 (2005).

M. Kumamoto et al., "Effects of pH and Metal Ions on Antioxidative Activities of Catechins," Biosci. Biotechnol. Biochem. 64(1):126-132 (2001).

E. Sergediene et al., "Prooxidant toxicity of polyphenolic antioxidants to HL-60 cells: description of quantitative structure-activity relationships," FEBS Letters 462:392-396 (1999).

K. Satoh et al., "Copper, but not Iron, Enhances Apoptosis-Inducing Activity of Antioxidants," Anticancer Research 17:2487-2490 (1997).

N. Sakuguchi et al., "Reactive Oxygen Species and Intracellular $Ca^{2+}$, Common Signals for Apoptosis Induced by Gallic Acid," Biochemical Pharmacology 55:1973-1981 (1998).

D. Bock et al., "Innovative Strategy in inflammatory Diseases," New Drugs D04(28):28-30 (2003).

E. Aydt et al., "Development of Synthetic Pan-Selectin Antagonists: A New Treatment Strategy for Chronic Inflammation in Asthma," Pathobiology 70:297-301 (2002-2003).

N.V. Bovin, "Neoglycoconjugates: trade and art," Biochem. Soc. Symp. 69:143-160 (2002).

N.V. Bovin, "Polyacrylamide-based blycoconjugates as tools in glycobiology," Glycoconjugate Journal 15:431-446 (1998).

T.V. Pochechueva et al., "P-Selectin Blocking Potency of Multimeric Tyrosine Sulfates In Vitro and In Vivo," Bioorganic & Medicinal Chemistry Letters 13(10):1709-1712 (2003).

G. Weitz-Schmidt et al., "An E-Selectin Binding Assay Based on a Polyacrylamide-Type Glycoconjugate," Analytical Biochemistry 238:184-190 (1996).

T. Nomoto et al., "Preparation of hydroxybenzamide derivatives as prevention and treatment agents for bone diseases," Chemical Abstracts + Indexes, American Chemical Society 125(13):XP002047512 (Sep. 23, 1996).

C.C.M. Appledoorn et al., "Rational Optimization of a Short Human P-selectin-binding Peptide Leads to Nanomolar Affinity Antagonists," Journal of Biological Chemistry 278(12)10201-10207, XP0022757 10 (Mar. 21, 2003).

R. Yamazaki et al., "Diarylheptanoids suppress expression of leukocyte adhesion molecules on human vascular endothelial cells," European Journal of Pharmacology 404(3):375-385, XP009062460 (Sep. 22, 2000).

C.C.M. Appledoorn et al., "Gallic Acid Antagonizes P-Selectin-Mediated Platelet-Leukocyte Interactions, Implications for the French Paradox," Circulation 111:106-112 (Jan. 2005).

N. Kaila et al., "Quinic Acid Derivatives as Sialyl Lewi$^x$s-Mimicking Selectin Inhibitors: Design, Synthesis, and Crystal Structure in Complex with E-Selectin," J. Med. Chem. 48:4346-4357 (2005).

D.H. Slee et al., "Development af Potent Non-Carbohydrate Imidazole-Based Small Molecule Selectin Inhibitors with Antiinflammatory Activity," J. Med. Chem. 44:2094-2107 (2001).

P.T. Mannisto et al., "Catechol-O-methyltransferase (COMT): Biochemistry, Molecular Biology, Pharmacology, and Clinical Efficacy of the New Selective COMT Inhibitors," Pharmacological Reviews, The American Society for Pharmacology and Experimental Therapeutics 51(4):593-628 (1999).

J. Axelrod et al., "Enzymatic O-Methylation of Epinephrine and Other Catechols," J. Biol. Chem. 223(3):702-705 (1958).

N. Haramaki et al., "Role af Ascorbate in Protection by Nitecapone Against Cardiac Ischemia—Reperfusion Injury," Biochemical Pharmacology 50(6):839-843 (1995).

E. Nissinen et al., "The COMT inhibitor, entacapone, reduces levedopa-induced elevations in plasma homocysteine in healthy adult rats," J. Neural. Transrn. 112:1213-1221 (2005).

Y.J. Suzuki et al., "Antioxidant Properties of Nitecapone (OR-462)," Free Radical Biology & Medicine 13:517-525 (1992).

L. Marcocci et al., "Nitecapone: A Nitric Oxide Radical Scaventer," Biochemistry and Molecular Biology International 34(3):531-541 (Oct. 1994).

T. Helkamaa et al., "Entacapone protects from angiotensin II-induced inflammation and renal injury," Journal of Hypertension 21:2353-2363 (2003).

M. Friedrich et al., "Pan-selectin antagonism improves psoriasis manifestation in mice and man," Arch Dermatol Res. 297:345-351, XP002370636 (2006).

Van De Waterbeemd H et al., "Property-Based Design: Optimization of Drug Absorption and Pharmacokinetics," J. Med. Chem. 44(9):1313-1333 (2001).

Harvey et al., "The results of five coded compounds: genistein, metaproterenol, rotenone, p-anisidine and resorcinol tested in the pH 6.7 Syrian hamster embryo cell morphological transformation assay," Mutagenesis 20(1):51-56 (2005).

Jan. 8, 2010, Office Action in U.S. Appl. No. 12/067,341.

Nov. 18, 2009, Office Action in U.S. Appl. No. 12/067,059.

Jul. 29, 2010, Office Action in U.S. Appl. No. 12/067,059.

Jul. 30, 2010, Office Action in U.S. Appl. No. 12/066,757.

Feb. 14, 2011, Office Action in U.S. Appl. No. 12/066,757.

Blaakmeer et al., "Structure-Activity Relationship of Isolated Avenanthramide Alkaloids and Synthesized Related Compounds as Oviposition Deterrents for Pieris Brassicae," J. Nat. Prods. 57(8):1145-1151 (1994).

Patani et al., "Bioisosterism: A Rational Approach in Drug Dosing," Chem. Rev. 96(8):3147-3176 (1996).

Merck Online Manuals, Chrohn's Disease, Revision Jan. 2007, by David B. Bachar MD.

STN Database Accession No. 1961:22545, English language abstract for Shingaki, T., "Reaction of substituted benzazides with benzylamine," *Nippon Kagaku Zasshi* 80:55-58, Nippon Kagakukai (1959).

STN Database, Accession No. 1961:22544, English language abstract for Slyusarev, A.T. and Gershuns, A.L., "Gallic acid anilides," *Ukrains'kii Khernichnii Zhur.* 26:364-367, Naukova Dumka (1960).

STN Database Accession No. 1962:446635, English language abstract for Manning, D.L. and Blander, M., "Association constants of silver (I) and cyanide ions in molten equimolar sodium nitrate-potassium nitrate mixtures," *Inorg. Chem.* 1:594-599, American Chemical Society (1962).

STN Database Accession No. 1962:446636, English language abstract for Slyusarev, A.T. and Gershuns, A. L., "Dissociation of p-carboxygallanilide," *Ukrainskii Khirnicheskii Zhur.* 28:309-315, Naukova Dumka (1962).

STN Database Accession No. 1964:86480, English language abstract for Lapin, N.N., and Efimenko, A.G., "Determination of titanium in heat-resistant steels," *Sb. Nauchn. Tr. Zhdanovsk. Met. Inst.* 9:103-107 (1963).

STN Database Accession No. 1964:428806, English language abstract for Slyusarev, A.T. and Gershuns, A. L., "Dissociation of p-carboxygallic anilide," *Inst. Khirn.* 133:95-103 (1963).

STN Database Accession No. 1972:85515, English language abstract for Morlyan, N.M. et al., "N-(3,4,5-Trimethoxybenzoyl)-p-aminobenzoic acid," *Metody Poluch. Khirn. Reaktiv. Prep.* 20:121-123 (1969).

STN Database Accession No. 1976:536659, English language abstract for Paschenko, E.N. et al., "Photometric determination of molybdenum in tungsten and its alloys as a carboxygallanilide complex," *Zhur. Anal. Khirnii* 31:400-401, lzd—vo Akademii Nauk SSR (1976).

STN Database, Accession No. 1975:612201, English language abstract for Russian Patent No. SU 480 000 (1975).

STN Database, Accession No. 1987:467992, English language abstract for Japanese Patent No. JP 61 282839 (1986).

STN Database, Accession No. 1990:45554, English language abstract for Japanese Patent No. JP 01 120554 (1989).

Beilstein Database, Registry No. 2763456, "N-(4-dimethylamino-phenyl)-3,4,S-trihydroxy-benzamide," Beilstein Institut zur Foerderung der Chemischen Wissenchaften, 2 pages (1989-1992).
Beilstein Database, Registry No. 2765383, "N-(4-diethylamino-phenyl)-3,4,5-trihydroxy-benzamide," Beilstein Institut zur Foerderung der Chemischen Wissenchaften, 2 pages (1989-1992).
International Search Report for International Application No. PCT/EP2005/002920, European Patent Office, Netherlands, mailed on Jun. 15, 2005.

Jun. 15, 2009, Office Action in U.S. Appl. No. 10/593,259.
Dec. 11, 2009, Office Action in U.S. Appl. No. 10/593,259.
Aug. 6, 2010, Office Action in U.S. Appl. No. 10/593,259.
Mar. 16, 2011, Office Action in U.S. Appl. No. 10/593,259.
Oct. 5, 2011, Office Action in U.S. Appl. No. 10/593,259.
English-language abstract of JP 10-306024, 1998.

* cited by examiner

AROMATIC COMPOUNDS AND THEIR USE IN MEDICAL APPLICATIONS

The present invention relates to compounds, compositions and methods for modulating the in vitro and in vivo processes mediated by cell adhesion molecules. The disclosed small molecules comprise trimethoxy phenyl subunits and modulate cell adhesion molecule-mediated functions potently.

Cell-adhesion molecule-mediated functions are part of a complex cascade leading to the migration of circulating white blood cells (leukocytes) from the blood stream into the surrounding tissue (transmigration). Physiologically, leukocyte transmigration is of critical importance for homeostasis and immuno-surveillance of living beings including humans. Lymphocytes for example, are constitutively leaving the blood stream into lymphatic tissues in order to patrol for harmful antigens. Under pathological circumstances however, e.g. local or systemic inflammation and/or injury of the vascular system, this fundamental process is dys-regulated, at least in part, due to an increased surface expression of E- and P-selectin. Consequently, the excessive leukocyte transmigration leads to a pathological cellular infiltrate with subsequent tissue damage in several clinically relevant settings. Disease states such as Acute Lung Injury (ALI), Acute Respiratory Distress Syndrome (ARDS), Asthma bronchiale (asthma), Chronic Obstructive Pulmonary Disease (COPD), Psoriasis, Rheumatoid Arthritis, and Sepsis are all associated with tissue inflammation induced and perpetuated by pathologically activated leukocytes infiltrating the respective tissue. In addition, exaggerated leukocyte infiltration contributes to the pathogenesis of Ischemic-Reperfusion Injury (IRI) associated with organ transplantation, cardiopulmonary bypass or percutaneous transluminal angioplasty.

To transmigrate, leukocytes must bind to the wall of the vascular endothelium to diffuse through the cell wall of the capillary into the surrounding tissue. Therefore, leukocytes have to roll onto and then adhere to the endothelial cell wall (initial rolling or "tethering"). This primary event in transmigration is mediated by the selectin family of cell-adhesion molecules. In addition to directly binding to the endothelium, leukocytes can adhere to other leukocytes, leukocyte-particles, platelets or platelet-derived particles that are already attached to the endothelium.

The selectin family of adhesion molecules is comprised of three structurally related calcium-dependent carbohydrate binding cell surface proteins, E-, P- and L-selectin. E-selectin is expressed only on inflamed endothelium, P-selectin is expressed on inflamed endothelium as well as on platelets and L-selectin is expressed on leukocytes. Selectins are composed of an amino terminal lectin domain, an epidermal growth factor (EGF)-like domain, a variable number of complement receptor-related repeats, a hydrophobic transmembrane domain and a C-terminal cytoplasmic domain. The binding interactions leading to the adhesion of the leukocytes are supposed to be mediated by contact of the lectin domain of the selectins and various carbohydrate ligands on the surface of the leukocytes. All three selectins can bind with low affinity to the carbohydrate sialyl Lewis$^x$ (sLe$^x$), a glycosyl moiety present on the surface of most leukocytes. A structurally related glycosyl moiety, sialyl Lewis$^a$ (sLe$^a$), is predominantly found on the surface of cancer cells [K. Okazaki et al., *J. Surg. Res.,* 1998, 78(1). 78-84; R. P. McEver et al., *Glycoconjugate Journal,* 1997, 14(5), 585-591]. In case of P-selectin, a distinct high affinity glycoprotein ligand has been described [R. P. McEver, R. D. Cummings, *J. Clin. Invest.,* 1997, 100, 485-492], the so-called P-selectin glycoprotein ligand-1 (PSGL-1), which contributes to a high affinity selectin binding by its sLe$^x$ moiety as well as by parts of its peptide components, in particular sulphated tyrosine residues [R. P. McEver, *Ernst Schering Res. Found. Workshop,* 2004, 44, 137-147]. PSGL-1 is one of the most important selectin ligands binding with highest affinity to P-selectin, but it also binds to E- and L-selectin [G. Constantin; *Drug News Perspect;* 2004; 17(9); 579-586]. It is a homodimeric sialomucin predominantly expressed on leukocytes.

In inflammatory diseases, dys-regulated transmigration is, at least in part, mediated due to an increased cell surface expression of E- and P-selectin. In contrast to their low basal expression, E- and P-selectin expression is upregulated during inflammation, leading to a substantial recruitment of leukocytes into the inflamed tissue. Although selectin-mediated cell adhesion is required for fighting infection, there are various situations in which such cell adhesion is undesirable or excessive, resulting in severe tissue damage instead of repair. In the case of many acute as well as chronic inflammatory disorders [e.g., asthma, chronic obstructive pulmonary disease (COPD), psoriasis, etc.], an association between infiltration of activated leukocytes into the tissue simultaneously with a marked elevation of tissue expression of corresponding adhesion molecules, particularly E- and P-selectin, has been demonstrated [Muller et al., *J. Pathol.,* 2002, 198(2), 270-275; Di Stefano et al., *Am. J. Respir. Crit. Care. Med.,* 1994, 149(3) 803-810; Terajima et al., *Arch. Dermatol. Res.,* 1998, 290, 246-252]

Leukocyte infiltration may also play a role in inflammatory symptoms in the course of transplant and graft rejection. Also the process of blood clotting is further promoted by leukocyte-leukocyte and leukocyte-platelet binding, which occurs because leukocytes possess both L-selectin and its corresponding ligand PSGL-1 and can thus interact with themselves via PSGL-1, and they can also bind to platelets which carry P-selectin.

Therefore, the modulation of selectin-mediated cell adhesion and other selectin mediated functions, e.g. leukocyte activation, offers a promising possibility to interfere with and stop the inflammation cascade at a very early step. Small molecule selectin antagonists should modulate all three selectins simultaneously as pan-selectin-antagonists to circumvent possible redundancies between the selectins [M. Sperandio et al., *Vascular Disease Prevention,* 2004, 1, 185-195].

Besides sLe$^x$/sLe$^a$, the natural, high affinity ligand PSGL-1 is another template structure for the design of small molecule selectin antagonists. As compared to sLe$^x$/sLe$^a$, PSGL-1 shows high affinity for all three selectins. To find and to detect novel small molecule drugs that compete with PSGL-1 and PSGL-1-like ligands for selectin binding is therefore a promising strategy to develop a novel class of effective pan-selectin antagonists for treating inflammatory disorders. Selectin antagonists may be designed using selectins as well as using a ligand like PSGL-1 as a template structure, since they are intended to modulate the binding between selectins and PSGL-1 or other ligands with similar binding motifs.

Novel small molecule selectin antagonists could meet certain requirements to be drug-like and to have potential oral bioavailability. The term drug likeness is described in the literature [Lipinski; *Adv. Drug Dev. Rev.,* 1997, 23, 3-25]. Beside other molecular properties, passively transported molecules are supposed to have on average a relative molecular weight of less than 500 in order to be drug like. According to these rules it is common to define compounds with a relative molecular weight of less 500 or closely above that as small molecules. Compounds with relative molecular weights above 500 are unlikely to be orally bioavailable. Also the presence of highly polar carbohydrate moieties or a peptidic components is not in accordance with the concept of drug likeness [H. Ulbrich et al., *Trends PharmacoL Sci.*, 2003, 24(12), 640-647; D. Slee et al., *J. Med. Chem.*, 2001, 44, 2094-2107]. The same accounts for the development of antibody-based drugs; because they are polypeptides and so oral administration is a problem. Moreover, the desired compounds must be stable during the passage through the gastrointestinal tract so that they can be ingested/absorbed latest by the cells of the small intestines. This is not the case for most glycosidic molecules and peptidic structures.

There have been various investigations to develop low-molecular weight compounds with an modulatory effect on selectin mediated processes. These compounds include disalicylates and disalicylate-based C-glycosides [WO 99/29706], benzyl amino sulfonic acids [WO 03/097658], diglycosylated 1,2-diols [WO 97/01569], substituted 5-membered heterocycles [WO 00/33836], mannopyranosyloxy-phenyl-benzoic acids [EP0758243 B1], piperazine based compounds [U.S. Pat. No. 6,432,957B1], gallic acid derivatives of peptides [WO 2004/018502], gallic acid [C. C. M. Appeldoorn et al., *Circulation* 2005, 111, 106-112; EP 1481669A1], and quinic acid derivatives [N. Kaila et al., *J. Med. Chem.* 2005, 48, 4346-4357]. However, none of these selectin-antagonizing compounds have successfully passed clinical trials up to date [S. J. Romano, *Treat. Respir Med* 2005, 4(2), 85-94; M. P. Schön, *Therapeutics and Clinical Risk Management*, 2005, 1(3), 201-208]. This is due to the fact, that many of these structures have been designed on the basis of the low potency template sLe$^x$. Therefore, sLe$^x$-mimicking structures are likely to show low potency. Other compounds show specificity against different members of the selectin family, but antagonizing only selected selectins can be bypassed by other selectins [M. P. Schön, *Therapeutics and Clinical Risk Management*, 2005, 1(3), 201-208]. In addition, most of the compounds developed so far have high molecular weights and often bear carbohydrates and/or peptides making them prone to degradation and modification by peptidases and/or glycosidases. Carbohydrate-bearing structures have further disadvantages such as high degree of chirality, anomericity, and low probability of transport through lipid bilayers. Similar disadvantages are known for peptide-bearing compounds. Some other compounds developed for antagonizing selectin mediated processes contain pyrogallol- and catechol-substructures. These motifs are prone to oxidation processes [Kumamoto M. et al., *Biosci. Biotechnol. Biochem.*, 2001, 65(1), 126-132] making the pharmaceutical development of these compounds difficult. In addition, compounds with pyrogallol substructures, such as gallic acid, are known to be cytotoxic [E. Sergediene et al., *FEBS Letters*, 1999, 462, 392-396] and induce apoptosis [K. Satoh et al., *Anticancer Research*, 1997, 17, 2487-2490; N. Sakaguchi et al., *Biochemical Pharmacology*, 1998, 55, 1973-1981].

The leading compound in the field of selectin antagonists is bimosiamose [S. J. Romano, *Treat. Respir Med* 2005, 4(2), 85-94]. Presently bimosiamose [D. Bock et al., *New Drugs*, 2003, D04, 28, p. 28; EP 0 840 606 B1] is the most advanced compound in clinical studies Recent investigations support the hypothesis that bimosiamose can be considered as PSGL-1 mimetic [E. Aydt, a Wolff; *Pathobiology;* 2002-2003; 70; 297-301]. This distinguishes bimosiamose from other selectin antagonists. It is, however, a high molecular weight compound with carbohydrate structures. The pan-selectin antagonist bimosiamose seems to lack oral bioavailability. Some observations indicate that bimosiamose shows good affinity for P-selectin and a moderate affinity for E- and L-selectin.

There is a strong medical need for novel highly potent pan-selectin antagonists which modulate selectin-mediated function, e.g. of selectin-dependent cell adhesion, and for the development of methods employing such compounds to modulate conditions associated with selectin-ligand interaction. Most of the available anti-inflammatory pharmaceutical therapies, which are available on the market, comprise mostly corticosteroids or NSAIDs (non steroidal anti-inflammatory drugs) having several serious drawbacks/side effects, and target different steps of the inflammatory cascade. Unlike this, modulating the selectin function is a therapeutic concept intervening the inflammation cascade at a very early stage. Almost all promising selectin antagonists so far failed to become marketed drugs, mostly because of low potency and/or high molecular weight that causes problems in their absorption-distribution-metabolism-excretion (ADME) behaviour and thus in oral bioavailability required for the treatment of most inflammatory disorders like rheumatoid arthritis, septic shock, atherosclerosis, reperfusion injury and many others.

Object of the invention is to provide novel small molecules, especially non-glycosylated/non-glycosidic and non-peptidic compounds, which are able to potently to antagonize selectin-mediated processes and which have less negative side effects during their application than prior art compounds.

Unlike most of the sLe$^x$-mimicking compounds developed in this field, the inventive compounds are not prone to glycosidases or peptidases. Most of the selectin antagonists developed so far are structurally and biologically based on the properties of sLe$^x$ or sLe$^a$. These resulting compounds showed, therefore, low biological activity like their template structures. This invention, however, provides novel potent small and drug like pan-selectin antagonists that have been invented on the basis of biological in vitro assays mimicking PSGL-1 and PSGL-1-like ligands or any ligands bearing sLe$^x$ or sLe$^a$ and tyrosinesulfate motifs [N. V. Bovin; *Biochem Soc Symp.;* 2002; (69):143-60. N. V. Bovin; *Glycoconj. J.;* 1998; 15(5); 431-46. T. V. Pochechueva et al.; *Bioorg Med Chem Lett.;* 2003; 13(10); 1709-12. G. Weitz-Schmidt et al.; *Anal. Biochem.;* 1996; 238; 184-190].

The present invention provides pharmaceutical compositions comprising at least one compound having the general structure of formulas (Ia) or (Ib) and a pharmaceutically acceptable carrier which is useful in medicine.

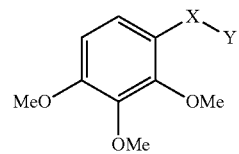

Ia

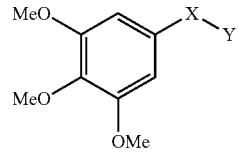

Ib wherein the symbols and substituents have the following meaning

—X—=

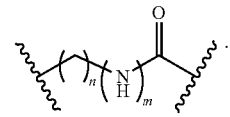

(a)

with m=0, 1; n=an integer from 1 to 3

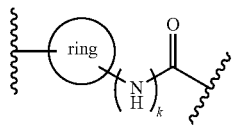
(b)

wherein "ring" is

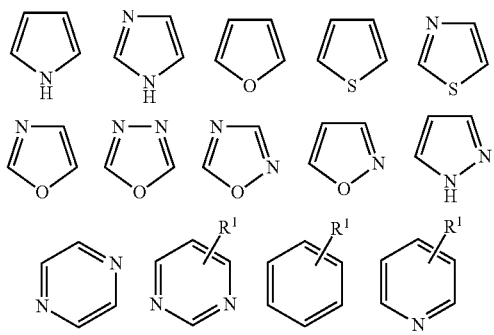

and with $R^1$ being H, $NO_2$, $CP_3$, F, Cl, Br, I, CN, $CH_3$, $NH_2$, NHAlkyl, NHAryl, NHAcyl and k=0, 1

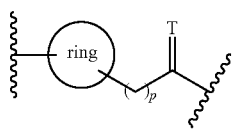
(c)

T being O, S or [H,H]; p=0, 1, 2,

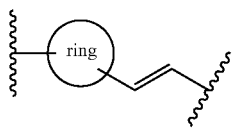
(d)

the double bond is either R- or Z-configurated

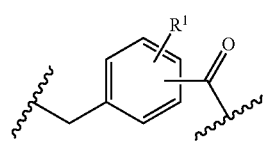
(e)

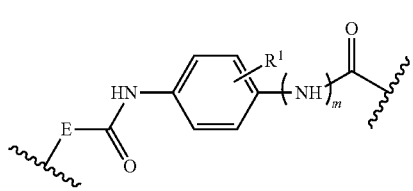
(f)

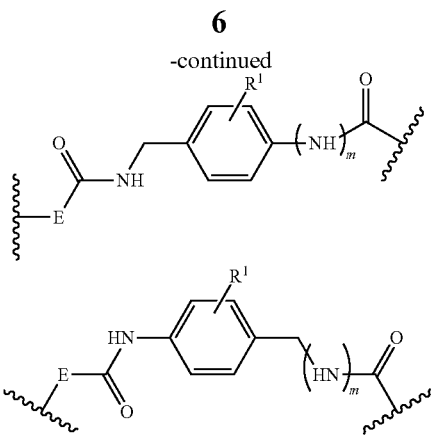

with -E- being —$(CH_2)_q$NH— and q=0, 1, 2, 3
—Y=

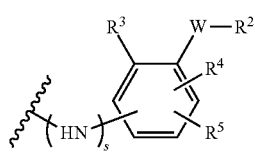
(a)

with s being 0 or 1,
$R^2$ being $CO_2H$, $CO_2Alkyl$, $CO_2Aryl$, $CO_2NH_2$, $CO_2Aralkyl$, $SO_3H$, $SO_2NH_2$, $PO(OH)_2$, 1-H-tetrazolyl-, CHO, $COCH_3$, $CH_2OH$, $NH_2$, NHAlkyl, N(Alkyl)Alkyl', $OCH_3$, $CH_2OCH_3$, SH, F, Cl, Br, I, $CH_3$, $CH_2CH_3$, CN, $CF_3$
$R^3$ independently from $R^2$ being H, $CH_3$, $CH_2CH_3$, $CF_3$, F, Cl, Br, I, CN, $NO_2$ and
$R^4$ independently from $R^2$ and $R^3$ being H, $CH_3$, $CH_2CH_3$, $CF_3$, F, Cl, Br, I, CN, $NO_2$, $R^2$
$R^5$ being H, $NO_2$, $CF_3$, F, Cl, Br, I, CN, $CH_3$, $OCH_3$, SH, $NH_2$
and —W—=—$(CH_2)_v$, cis-CH=CH— or trans-CH=CH—, and v being 0, 1, 2;
in case that —W— is cis-CH=CH— or trans-CH=CH—, $R^2$ must not be $NH_2$ or SH;

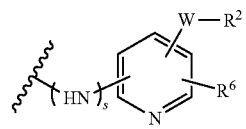
(b)

$R^6$ independently from $R^2$ being H, F, Cl, Me, tert-Bu, CN,

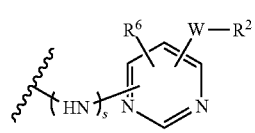
(c)

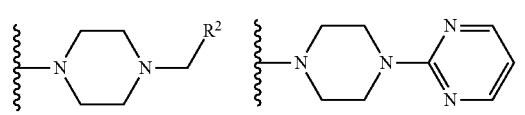
(d)

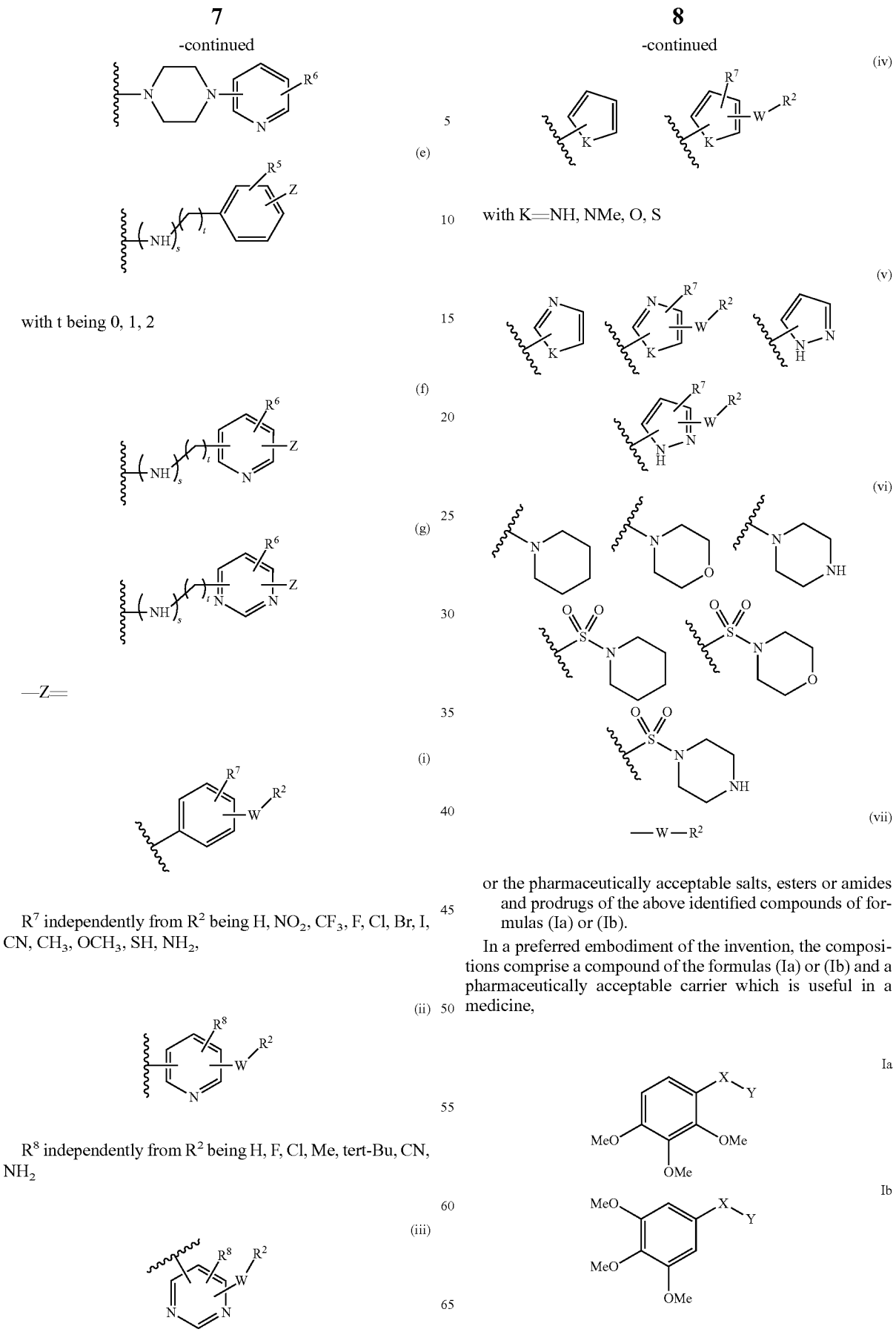

with t being 0, 1, 2

—Z=

R[7] independently from R[2] being H, NO$_2$, CF$_3$, F, Cl, Br, I, CN, CH$_3$, OCH$_3$, SH, NH$_2$, R[8] independently from R[2] being H, F, Cl, Me, tert-Bu, CN, NH$_2$ with K=NH, NMe, O, S or the pharmaceutically acceptable salts, esters or amides and prodrugs of the above identified compounds of formulas (Ia) or (Ib).

In a preferred embodiment of the invention, the compositions comprise a compound of the formulas (Ia) or (Ib) and a pharmaceutically acceptable carrier which is useful in a medicine, wherein the symbols, indices and substituents have the following meaning —X=

(a)

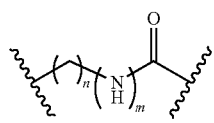

with m=0, 1; n=an integer from 1 to 3

(b)

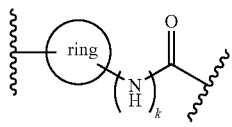

to wherein "ring" is

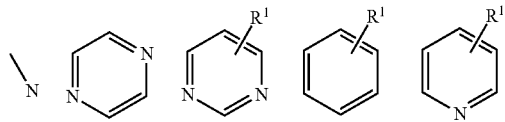

and with $R^1$ being H, $NO_2$, $CF_3$, F, Cl, Br, I, CN, $CH_3$, $NH_2$, NHAlkyl, NHAryl, NHAcyl and k=0, 1

(c)

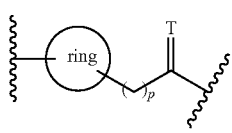

T being O, S or [H,H]; p=0, 1, 2,
—Y=

(a)

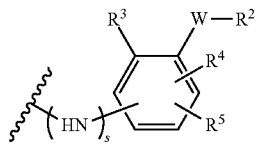

with s being 0 or 1,
$R^2$ being $CO_2H$, $CO_2Alkyl$, $CO_2Aryl$, $CO_2NH_2$, $CO_2Aralkyl$, $SO_3H$, $SO_2NH_2$, $PO(OH)_2$, 1-H-tetrazolyl-, CHO, $COCH_3$, $CH_2OH$, $NH_2$, NHAlkyl, N(Alkyl)Alkyl', $OCH_3$, $CH_2OCH_3$, SH, F, Cl, Br, I, $CH_3$, $CH_2CH_3$, CN, $CF_3$
$R^3$ independently from $R^2$ being H, $CH_3$, $CH_2CH_3$, $CF_3$, F, Cl, Br, I, CN, $NO_2$ and
$R^4$ independently from $R^2$ and $R^3$ being H, $CH_3$, $CH_2CH_3$, $CF_3$, F, Cl, Br, I, CN, $NO_2$, $R^2$
$R^5$ being H, $NO_2$, $CF_3$, F, Cl, Br, I, CN, $CH_3$, $OCH_3$, SH, $NH_2$
and —W—=—$(CH_2—)_v$, cis-CH=CH— or trans-CH=CH—, and v being 0, 1, 2;
in case that —W— is cis-CH=CH— or trans-CH=CH—, $R^2$ must not be $NH_2$ or SH;

(e)

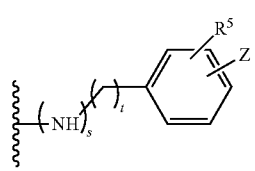

with t being 0, 1, 2

—Z=

(i)

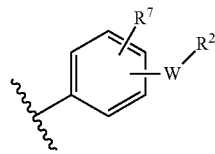

$R^7$ independently from $R^2$ being H, $NO_2$, $CF_3$, F, Cl, Br, I, CN, $CH_3$, $OCH_3$, SH, $NH_2$, (iv)

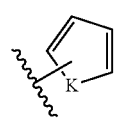

with K=NH, NMe, O, S or the pharmaceutically acceptable salts, esters or amides and prodrugs of the above identified compounds of formulas (Ia) or (Ib).

Preferred pharmaceutical compositions comprise compounds of formulas (IIa) or (IIb)

IIa

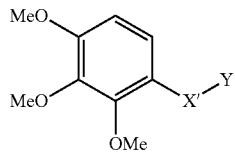

IIb

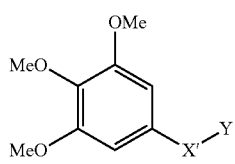

wherein —Y is like defined above and wherein —X'— is X (a), X(b), X(c), and X(d) like defined above. Preferred definitions of —X'— are X(a), X(b) and X(c), more preferred are X(b) and X(c).

Further preferred pharmaceutical compositions comprise compounds of formulas (A1), (B1), (A2) or (B2)

A1

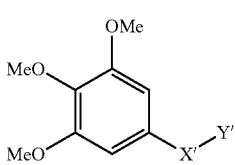

A2

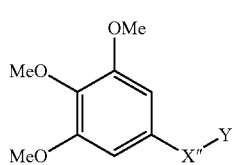

B1

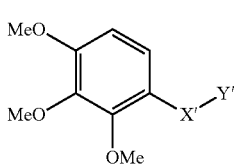

-continued

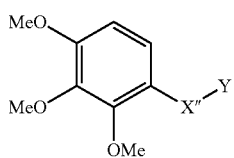

wherein —X'— and —Y are like defined above and wherein —X"— is

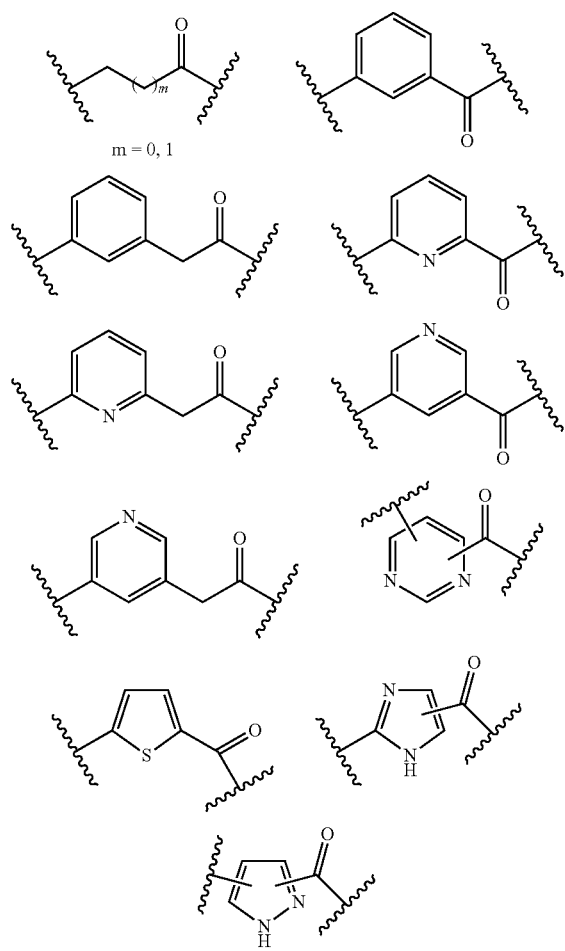

and wherein —Y' is

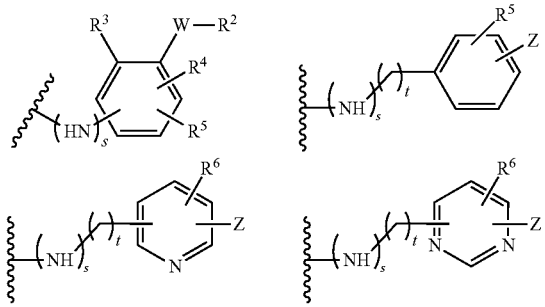

-continued

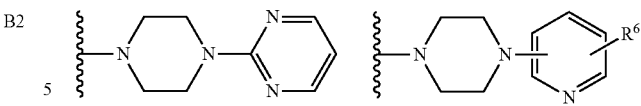

wherein all indices, symbols and substituents are like defined above.

In a further embodiment of the invention, the compounds of the formulas A1, A2, B1 and B2 are used, wherein —X'— and —Y are as defined as above and wherein —X"— is

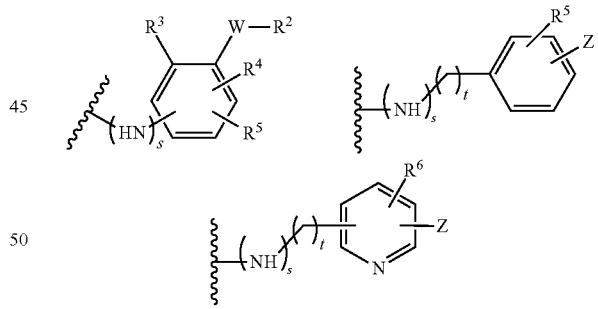

and wherein —Y' is and wherein all other indices, symbols and substituents are as defined above.

Particularly preferred pharmaceutical compositions comprise compounds of formulas (C) and (D)

-continued

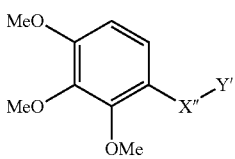

wherein —X"— and —Y' are like defined above.

Very particularly preferred pharmaceutical compositions comprise at least one compound of formulas (E) and (F)

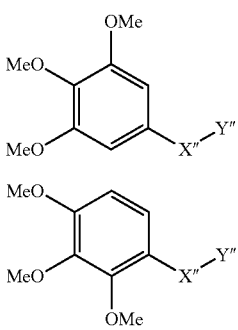

wherein —X"— is like defined above and —Y" is

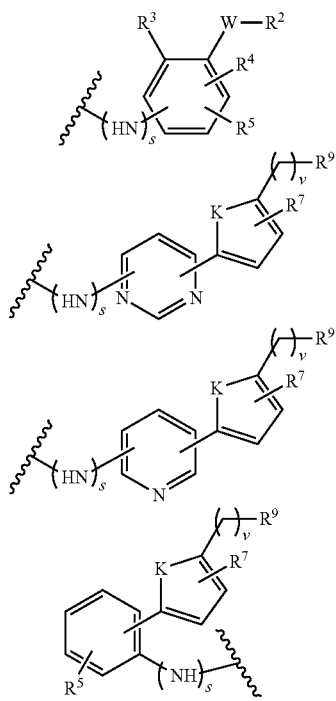

with $R^9$ being $CO_2H$, $CO_2$alkyl, $CO_2$aryl, $CO_2NH_2$, $CO_2$aralkyl, $CH_2SO_3H$, $CH_2SO_2NH_2$, $CH_2PO(OH)_2$, 1-H-tetrazolyl, CHO, $COCH_3$, $CH_2OH$, $CH_2NH_2$, $CH_2$NHalkyl, $CH_2$N(alkyl)alkyl', $CH_2OCH_3$, $CH_2SH$, wherein the indices, symbols and substituents are defined as above.

The invention also relates to pharmaceutical compositions, wherein the compounds are defined by formulas (E) or (F)

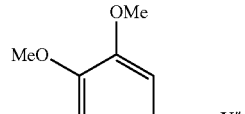

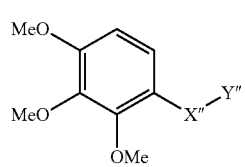

to wherein —X"— is as defined as above and —Y" is

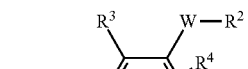

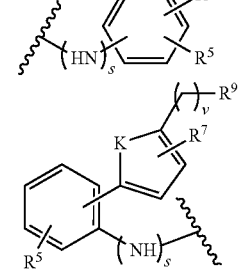

with $R^9$ being $CO_2H$, $CO_2$alkyl, $CO_2$aryl, $CO_2NH_2$, $CO_2$aralkyl, $CH_2SO_3H$, $CH_2SO_2NH_2$, $CH_2PO(OH)_2$, 1-H-tetrazolyl, CHO, $COCH_3$, $CH_2OH$, $CH_2NH_2$, $CH_2$NHalkyl, $CH_2$N(alkyl)alkyl', $CH_2OCH_3$, $CH_2SH$, wherein all other indices, symbols and substituents are as defined above.

These chemical compounds (C), (D), (E) and (F) are also new compounds for themselves.

All compounds as described before present the ability of modulating cell adhesion and modulate selectin- as well as PSGL-1-like mediated binding. The compounds have the ability to modulate the interaction of selectins with sLe$^x$/sLe$^a$ and also the interaction between selectins and tyrosinesulfate residues. Therefore they are useful for the treatment of acute and chronic inflammatory disorders, as well as other medical conditions where selectin mediated processes play a role.

The term "pharmaceutical" includes also diagnostic applications.

The term "pharmaceutical" includes also prophylactic applications in order to prevent medical conditions where selectin mediated processes play a role.

The term "pharmaceutical" includes also applications, where compounds of the present invention may be used as vehicles for drug targeting of diagnostics or therapeutics.

The invention provides pharmaceutical compositions comprising compounds of formulas (Ia) or (Ib) and in a preferred variant of formulas (IIa) or (IIb).

In a further preferred variant the invention provides pharmaceutical compositions comprising at least one compound of formula (A1), (A2), (B1) or (B2).

In a particularly preferred variant the invention provides pharmaceutical compositions comprising at least one compound of formula (C) or (D).

In a very particularly preferred variant the invention provides pharmaceutical compositions comprising at least one compound of formula (E) or (F).

The present invention further provides a method of modulating the binding of P-selectin, L-selectin or E-selectin to $sLe^x$ or $sLe^a$ and tyrosinesulfate residues comprising the step of administering to a patient an effective amount of at least one compound having the structure of formulas (Ia) or (Ib) to modulate the binding of P-, E- or L-selectin to $sLe^x$ or $sLe^a$ and tyrosinesulfate. It has been found that compounds having the formulas (Ia) or (Ib) shown above act to modulate E-, P- or L-selectin binding.

As used herein the terms "alkyl" shall mean a monovalent straight chain or branched chain group of 1 or 2 or 3 or 4 or 5 or 6 or 7 or 8 or 9 or 10 or 11 or 12 carbon atoms including, but not limited to, methyl, ethyl, n-propyl, isopropyl, n-butyl, sec-butyl, tert-butyl and the like. "Alkyl" is independently from each other and can be different or identical.

The term "aryl" shall mean carbocyclic and heterocyclic aromatic groups including, but not limited to, phenyl, 1-naphthyl, 2-naphthyl, fluorenyl, (1,2)-dihydronaphthyl, indenyl, indanyl, thienyl, benzothienyl, thienopyridyl and the like.

The term "aralkyl" (also called arylalkyl) shall mean an aryl group appended to an alkyl group including, but not limited to, benzyl, 1-naphthylmethyl, 2-naphthylmethyl, fluorobenzyl, chlorobenzyl, bromobenzyl, iodobenzyl, alkoxybenzyl (wherein "alkoxy" means methoxy, ethoxy, isopropoxy, n-butoxy, sec-butoxy, tert-butoxy an the like), hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The term "acyl" shall mean —(CHO) or —(C=O)-alkyl or —(C=O)-aryl or —(C=O)-aralkyl including, but not limited to, formyl, acetyl, n-propionyl, isopropionyl, n-butyryl, isobutyryl, pivaloyl, benzoyl, 4-nitrobenzoyl and the like.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgment, suitable for use in contact with tissues of patients without undue toxicity, irritation, allergic response and the like, commensurate with a reasonable benefit/risk ratio, and effective for their intended use, as well as the zwitterionic forms, where possible, of the compounds of the present invention. The term "salts" refers to the relatively non-toxic, inorganic and organic acid addition salts of the compounds of the present invention. These to salts can be prepared in situ during the final isolation and purification of the compounds or by separately reacting the purified compounds in its free form with a suitable inorganic or organic acid or base and isolating the salt thus formed. Representative salts of the compounds of the present invention include the hydrobromide, hydrochloride, sulfate, bisulfate, nitrate, acetate, oxalate, valerate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. These may include cations based on the alkali and alkaline earth metals, such as sodium, lithium, potassium, calcium, magnesium and the like, as well as non-toxic ammonium, quaternary ammonium and amine cations including, but not limited to, ammonium, tetramethylammonium, tetraethylammonium, methylamine, dimethylamine, trimethylamine, triethylamine, ethylamine, and the like.

Examples of the pharmaceutically acceptable, non-toxic esters of the compounds of this invention include $C_1$, $C_2$, $C_3$, $C_4$, $C_5$ and $C_6$ alkyl esters wherein the alkyl group is a straight or branched chain. Acceptable esters also include $C_5$, $C_6$ and $C_7$ cycloalkyl esters as well arylalkyl esters such as, but not limited to benzyl. $C_1$, $C_2$, $C_3$, $C_4$, $C_5$ and $C_6$ alkyl ester are preferred. Esters of the compounds of the present invention may be prepared according to conventional methods.

Examples of pharmaceutically acceptable, non-toxic amides of compounds of this invention include amides derived from ammonia, primary $C_1$, $C_2$, $C_3$, $C_4$, $C_5$ and $C_6$ alkyl amines and secondary $C_1$, $C_2$, $C_3$, $C_4$, $C_5$ and $C_6$ dialkyl amines wherein the alkyl groups are straight or branched chains. In the case of secondary amines the amine may also be in the form of a 5 or 6 membered heterocycle containing one nitrogen atom. Amides derived from ammonia, $C_1$, $C_2$ and $C_3$ alkyl primary amides and $C_1$ to $C_2$ dialkyl secondary amides are preferred. Amides of the compounds of the present invention may be prepared according to conventional methods.

The term "prodrug" refers to one or more compounds that are rapidly transformed in vitro and from a non-active to active state in vivo to yield the parent compound of the above formulas (Ia) or (Ib), for example by hydrolysis in blood or in vivo metabolism.

It is also contemplated that pharmaceutically active compositions may contain a compound of the present invention or other compounds that modulate or compete with E-selectin or P-selectin or L-selectin binding.

Pharmaceutically active compositions of the present invention comprise a pharmaceutically acceptable carrier and a compound of formulas (Ia) or (Ib), whereby a pharmaceutically acceptable carrier can also be a medically appropriate nano-particle, dendrimer, liposome, microbubble or polyethylene glycol (PEG). The pharmaceutical compositions of the present invention may include one or more of the compounds having the above structure (Ia) or (Ib) formulated together with one or more, physiologically acceptable carriers, adjuvants or vehicles, which are collectively referred to herein as carriers, for parenteral injection, for oral administration in solid or liquid form, for rectal or topical administration and the like.

The compositions can be administered to humans and animals either orally, rectally, parenterally (intravenously, intramuscularly, intradermaly or subcutaneously), intracisternally, intravaginally, interperitoneally, locally (powders, ointments or drops), or as a buccal or by inhalation (nebulized, or as nasal sprays).

Compositions suitable for parenteral injection may comprise physiologically acceptable sterile aqueous or nonaqueous solutions, stabilizers, antioxidants, preservatives (e.g. ascorbic acid, sodium sulfite, sodium hydrogene sulfite, benzyl alcohol, EDTA), dispersions, suspensions or emulsions and sterile powders for reconstitution into sterile injectable solution or dispersion. Examples of suitable aqueous and nonaqueous carriers, diluents, solvents or vehicles include water, ethanol, polyol, (propylene glycol, polyethylene glycol, glycerol and the like), suitable mixtures thereof, vegetable oils (such as olive or canola oil) and injectable organic esters such as ethyl oleate. Proper fluidity can be maintained, for examples, by the use of a coating such as lecithin, by the maintenance of the required particle size in the case of dispersions and by the use of surfactants.

These compositions may also contain adjuvants such as preserving, wetting, emulsifying, and dispersing agents. Prevention of the actions of microorganisms can be ensured by various antibacterial and antifungal agents, for examples, parabens, chlorobutanol, phenol, sorbic acid, and the like. It may also be desirable to include isotonic agents, for examples sugars, sodium chloride and the like. Prolonged absorption of the injectable pharmaceutical form can be brought about by the use of agents delaying absorption, for examples aluminium monostearate and gelatin.

If desired, and for more effective distribution, the compounds can be incorporated into slow or timed release or targeted delivery systems such as polymer matrices, liposomes, and microspheres. They may be sterilized, for example, by filtration through a bacteria-retaining filter, or by incorporating sterilizing agents in the form of sterile water, or some other sterile injectable medium immediately before use.

Solid dosage forms for oral administration include capsules, tablets, pills, powders and granules. In such solid dosage forms, the active compound or a prodrug is admixed with at least one inert customary excipient (or carrier) such as sodium citrate or dicalcium phosphate or (i) fillers or extenders, as for example, starches, lactose, sucrose, glucose, mannitol and silicic acid, (ii) binders, as for example, carboxymethylcellulose, alginates, gelatine, polyvinylpyrrolidone, sucrose and acacia, (iii) humectants, as for example, glycerol, (div disintegrating agents, as for example, agar-agar, calcium carbonate, potato or tapioca starch, aliginic acid, certain complex silicates and sodium carbonate, (v) solution retarders, as for examples, paraffin, (vi) absorption accelerators, as for example, quaternary ammonium compounds, (vii) wetting agents, as for examples, cetyl alcohol and glycerol monostearate, (viii) adsorbents, as for example, kaolin and bentonite, and (ix) lubricants, as for example, talc, calcium stearate, magnesium stearate, solid polyethylene glycols, sodium lauryl sulfate and mixtures thereof. In the case of capsules, tablets, and pills, the dosage forms may also comprise buffering agents.

Solid compositions of a similar type may also, be employed as fillers in soft and hard-filled gelatine capsules using excipients as lactose or milk sugars as well as high molecular polyethylene glycols and the like. Solid dosage forms such as tablets, dragées, capsules, pills and granules can be prepared with coatings and shells, such as enteric coatings and others well known in the art. They may contain opacifying agents, and can also be of such compositions that they release the active compound or compounds in a certain part of the intestinal tract in a delayed manner. Examples of embedding compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, cannola oil, caster oil and sesame seed oil, glycerol, tetrahydrofurfuryl alcohol, polyethylene glycols and fatty acid esters of sorbitan or mixtures of these substances, and the like. Besides such inert diluents, the compositions can also include adjuvants, such as wetting agents, emulsifying and suspending agents, sweeting, flavouring and perfuming agents.

Suspensions, in addition to the active compounds, may contain suspending agents, for example, ethoxylated isostearyl alcohols, polyoxyethylene sorbitol and sorbitan esters, microcrystalline cellulose, aluminium metahydroxide, bentonite, agar-agar, tragacanth or mixtures of these substances and the like.

Compositions for rectal administrations are preferably suppositories, which can be prepared by mixing the compounds of the present invention with suitable nonirritating excipients or carriers such as cacao butter, polyethylene glycol or a suppository wax, which are solid at ordinary temperatures but liquid at body temperature and therefore melt in the rectal or vaginal cavity and release the active component. Dosage forms for topical administration of a compound of this invention include ointments, powder, sprays and inhalants.

The active component is admixed under sterile conditions with a physiologically acceptable carrier and any needed preservatives, buffers or propellants as may be required. Ophthalmic formulations, eye ointments, suspensions, powder and solutions are also contemplated as being within the scope of this invention.

The compounds of the present invention can also be incorporated into or connected to liposomes or administrated in the form of liposomes. As is known in the art, liposomes are generally derived from phospholipids or other lipid substances. Liposomes are formed by mono or multilamellar hydrated liquid crystals that are dispersed in an aqueous medium. Any non-toxic, physiologically acceptable metabolized lipid capable of forming liposomes can be used. The present compositions in liposome form can contain, in addition to the selectin binding antagonists of the present invention, stabilizers, preservatives, excipients and the like. The preferred lipids are the phospholipids and the phosphatidyl cholines (lecithins), both natural and synthetic. Methods to form liposomes are well known in the art.

Non-parenteral dosage forms may also contain a bioavailability enhancing agent (e.g. enzyme modulators, antioxidants) appropriate for the protection of the compounds against degradation. Actual dosage levels of active ingredient in the composition of the present invention may be varied so as to obtain an amount of active ingredient that is effective to obtain the desired therapeutic response for a particular composition and method of administration. The selected dosage level, therefore, depends on the desired therapeutic effect, on the route of administration, on the desired duration of treatment and other factors. The total daily dosage of the compounds on this invention administered to a host in to single or divided doses may be in the range up to 50 mg per kilogram of body weight. Dosage unit compositions may contain such submultiples thereof as may be used to make up the daily dosage. It will be understood, however, that the specific dose level for any particular patient, whether human or other animal, will depend upon a variety of factors including the body weight, general health, sex diet, time and route of administration, rates of absorption and excretion, combination with other drugs and the severity of the particular disease being treated.

In particular, the compounds of the present invention may be used to treat a variety of diseases relating to inflammation and cell-cell recognition and adhesion. For example, the compounds of the present invention may be administrated to a patient to treat Chronic Obstructive Pulmonary Disease (COPD), acute lung injury (ALI), cardiopulmonary bypass, acute respiratory distress syndrome (ARDS), Crohn's disease, septic shock, sepsis, chronic inflammatory diseases such as psoriasis, atopic dermatitis, and rheumatoid arthritis, and reperfusion injury that occurs following heart attacks, strokes, atherosclerosis, and organ transplants, traumatic shock, multi-organ failure, autoimmune diseases like multiple sclerosis, percutaneous transluminal angioplasty, asthma and inflammatory bowel disease. In each case, an effective amount of the compounds of the present invention is administered either alone or as part of a pharmaceutically active composition to a patient in need of such treatment. It is also recognized that a combination of the compounds may be administered to a patient in need of such administration. The compounds of the present invention may also be administered to treat other diseases that are associated with cell-cell adhesion. As the present compounds modulate the binding of E-selectin or P-selectin or L-selectin, any disease that is related to this interaction may potentially be treated by the modulation of this binding interaction.

In addition to being found on some white blood cells, $sLe^a$ is found on various cancer cells, including lung and colon cancer cells. It has been suggested that cell adhesion involving $sLe^a$ may be involved in the metastasis of certain cancers and antagonists of $sLe^a$ binding might be useful in treatment of some forms of cancer.

The use of the active ingredients according to the invention or of cosmetic or topical dermatological compositions with an effective content of active ingredient according to the invention surprisingly enables effective treatment, but also prophylaxis of skin ageing caused by extrinsic and intrinsic factors.

The invention particularly relates to the use of a compound of formula (Ia) or (Ib) or a stereoisomeric form thereof for the preparation of a cosmetic or dermatological composition.

The amount used of the active compound or a stereoisomeric form thereof corresponds to the amount required to obtain the desired result using the cosmetic or dermatological compositions. One skilled in this art is capable of evaluating this effective amount, which depends on the derivative used, the individual on whom it is applied, and the time of this application. To provide an order of magnitude, in the cosmetic or dermatological compositions according to the invention, the compound of formula (Ia) or (Ib) or a stereoisomeric form thereof may be administered in an amount representing from 0.001% to 40% by weight, preferentially 0.005% to 30% by weight and more preferentially from 0.01% to 20% by weight.

A further aspect covers cosmetic compositions comprising a compound of formula (Ia) or (Ib) or a stereoisomeric form thereof and at least one cosmetically tolerable component, e.g. a cosmetically tolerable component for skin applications.

The amounts of the various components of the physiological medium of the cosmetic composition according to the invention are those generally included in the fields under consideration. When the cosmetic composition is an emulsion, the proportion of the fatty phase may range from 2% to 80% by weight and preferably from 5% to 50% by weight relative to the total weight of the cosmetic composition.

Thus, the cosmetic composition should contain a non-toxic physiologically acceptable medium that can be applied to human skin. For a topical application to the skin, the cosmetic composition may be in the form of a solution, a suspension, an emulsion or a dispersion of more or less fluid consistency and especially liquid or semi-liquid consistency, obtained by dispersing a fatty phase in an aqueous phase (O/W) or, conversely, (W/O), or alternatively a gel. A cosmetic composition in the form of a mousse or in the form of a spray or an aerosol then comprising a pressurized propellant may also be provided. Also the compositions may be in the form of a haircare lotion, a shampoo or hair conditioner, a liquid or solid soap, a treating mask, or a foaming cream or gel for cleansing the hair. They may also be in the form of hair dye or hair mascara.

The cosmetic compositions of the invention may also comprise one or more other ingredients usually employed in the fields under consideration, selected from among formulation additives, for instance aqueous-phase or oily-phase thickeners or gelling agents, dyestuffs that are soluble in the medium of the cosmetic composition, solid particles such as mineral or organic fillers or pigments in the form of microparticles or nanoparticles, preservatives, fragrances, hydrotopes or electrolytes, neutralizers (acidifying or basifying agents), propellants, anionic, cationic or amphoteric surfactants, polymers, in particular water-soluble or water-dispersible anionic, non-ionic, cationic or amphoteric film-forming polymers, mineral or organic salts, chelating agents; mixtures thereof.

The cosmetic compositions may be used to inhibit the micro-inflammatory cycle. Thus, the present invention also relates to cosmetic compositions comprising a compound of formula (Ia) or (Ib) or a stereoisomeric form thereof that is used for the cosmetic treatment or cosmetic prophylaxis of micro-inflammatory conditions.

Cosmetic compositions comprising a compound of formula (Ia) or (Ib) or a stereoisomeric form thereof that is used for the cosmetic treatment or cosmetic prophylaxis of skin ageing caused by intrinsic factors are also subject of the present invention. Intrinsic factors responsible for skin ageing are genetically programmed determinants including age, hormonal status, and psychological factors.

Beside cosmetically inactive ingredients the cosmetic compositions of the present invention may also comprise one or more cosmetically active ingredients with beneficial to action on the skin. Thus, the present invention relates to cosmetic compositions comprising a compound of formula (Ia) or (Ib) or a stereo isomeric form thereof and at least one further cosmetically active ingredient, e.g. an UV-blocker or proteins.

Dermatological compositions comprising a compound of formula (Ia) or (Ib) or a stereoisomeric form thereof and at least one dermatologically tolerable component, e.g. a dermatologically tolerable component for skin applications, are also subject of the invention.

Dermatologically tolerable components that can be used for the dermatological compositions described here are identical to the cosmetically tolerable components as defined in this invention.

A further embodiment of this invention are dermatological compositions comprising a compound of formula (Ia) or (Ib) or a stereoisomeric form thereof that is used for the dermatological treatment, dermatological diagnosis or dermatological prophylaxis of micro-inflammatory conditions.

In particular the invention covers dermatological compositions comprising a compound of formula (Ia) or (Ib) or a stereoisomeric form thereof that is used for the dermatological treatment, dermatological diagnosis or dermatological prophylaxis of itching and skin ageing caused by extrinsic factors. Extrinsic factors include environmental factors in general; more particularly photo-ageing due to exposure to the sun, to light or to any other radiation, atmospheric pollution, wounds, infections, traumatisms, anoxia, cigarette smoke, hormonal status as response to external factors, neuropeptides, electromagnetic fields, gravity, lifestyle (e.g. excessive consumption of alcohol), repetitive facial expressions, sleeping positions, and psychological stressors.

In addition to dermatologically inactive ingredients the dermatological compositions may also comprise dermatologically or pharmaceutically active ingredients. Thus, the present invention also relates to dermatological compositions comprising a compound of formula (Ia) or (Ib) or a stereoisomeric form thereof and at least one further dermatologi cally or pharmaceutically active ingredient. The dermatologically or pharmaceutically active ingredients that can be used for the dermatological compositions described herein are defined as the cosmetically active ingredients defined above. Dermatologically or pharmaceutically active ingredients can be identical to the cosmetically active ingredients as defined in this invention.

Another subject of the present invention are dermatological compositions comprising a compound of formula (Ia) or (Ib) or a stereoisomeric form thereof and at least one further dermatologically or pharmaceutically active ingredient characterized in that it is used for the dermatological treatment, dermatological diagnosis or dermatological prophylaxis of micro-inflammatory conditions.

In particular, the present invention relates to dermatological compositions comprising a compound of formula (Ia) or (Ib) or a stereoisomeric form thereof and at least one further dermatologically or pharmaceutically active ingredient characterized in that it is used for the dermatological treatment, dermatological diagnosis or dermatological prophylaxis of itching and skin ageing caused by extrinsic factors.

Ageing of the skin may also be caused by a combination of intrinsic and extrinsic factors. Therefore, the present invention also relates to dermatological compositions comprising a compound of formula (Ia) or (Ib) or a stereoisomeric form thereof and at least one further pharmaceutically or cosmetically active ingredient characterized in that it is used for the cosmetic and dermatological treatment and cosmetic and dermatological prophylaxis of skin ageing caused by a combination of intrinsic and extrinsic factors.

Another embodiment of this invention is a process for the preparation of a cosmetic composition by mixing a compound of formula (Ia) or (Ib) or a stereoisomeric form thereof, at least one cosmetically tolerable component and eventually further cosmetically active ingredients.

In particular, a process for the preparation of a cosmetic composition by mixing a compound of formula (Ia) or (Ib) or a stereoisomeric form thereof, at least one cosmetically tolerable component and eventually further cosmetically active ingredients, wherein the composition includes from 0.01% to 20% by weight of compound of formula (Ia) or Ib) or a stereoisomeric form thereof, based on the total weight of the composition is subject of this invention.

A further aspect deals with a process for the preparation of a dermatological composition by mixing a compound of formula (Ia) or (Ib) or a stereoisomeric form thereof, at least one dermatologically tolerable component and eventually further pharmaceutically active ingredients.

Many of the compounds of the present invention may be synthesized according to the following general synthetic schemes.

SCHEME 1

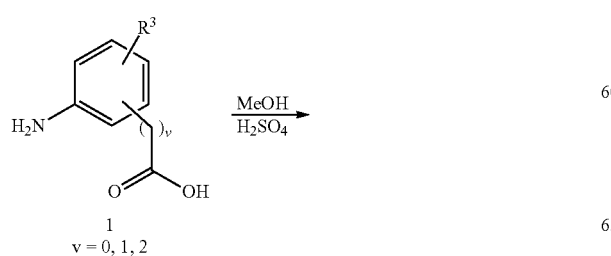

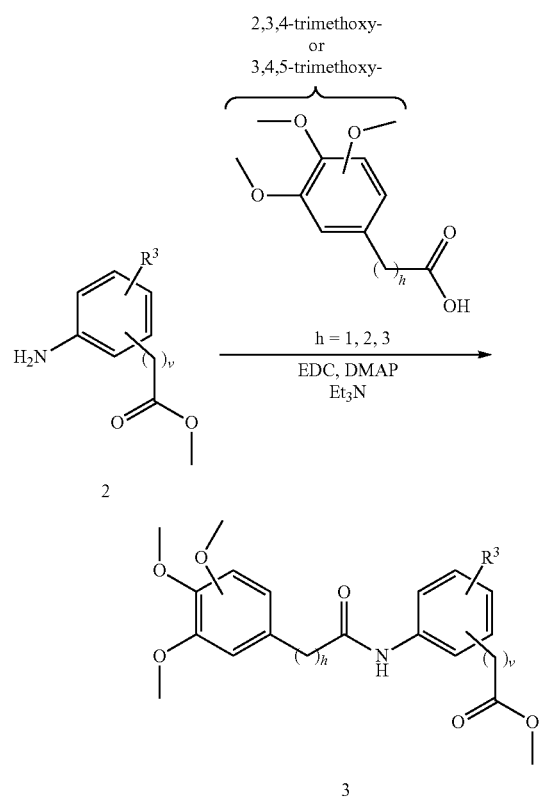

In SCHEME 1 an amino acid of type (1) is reacted to the corresponding methyl ester (2) under heating with acidic methanol. Ester (2) is reacted with a trimethoxy-phenyl-alkylic acid under state-of-the-art conditions (i.e. N'-(3-dimethylaminopropyl)-N-ethyl carbodiimide (EDC), triethylamine and 4-dimethylaminopyridine (DMAP) in a chlorinated solvent) to the amide (3). Alternatively diisopropyl carbodiimide (DIC) and hydroxybenzotriazole (HOBt) may be used for this reaction step. The synthesis sequence shown in SCHEME 1 leading to compounds like (3) is not only reduced to the Y-H building blocks like (1) but may be generally applied to all other Y-H type building blocks leading to compounds of type (A1), (A2), (B1) and (B2) as shown in the paragraph before.

SCHEME 2

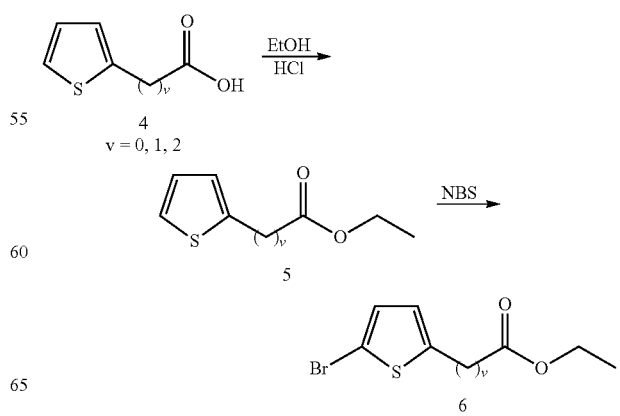

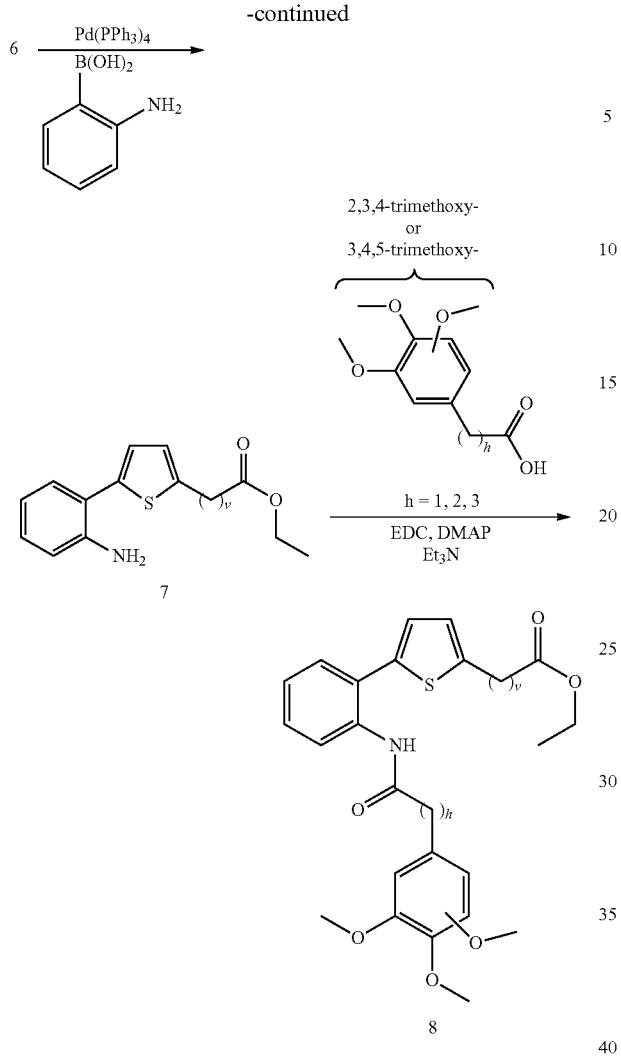
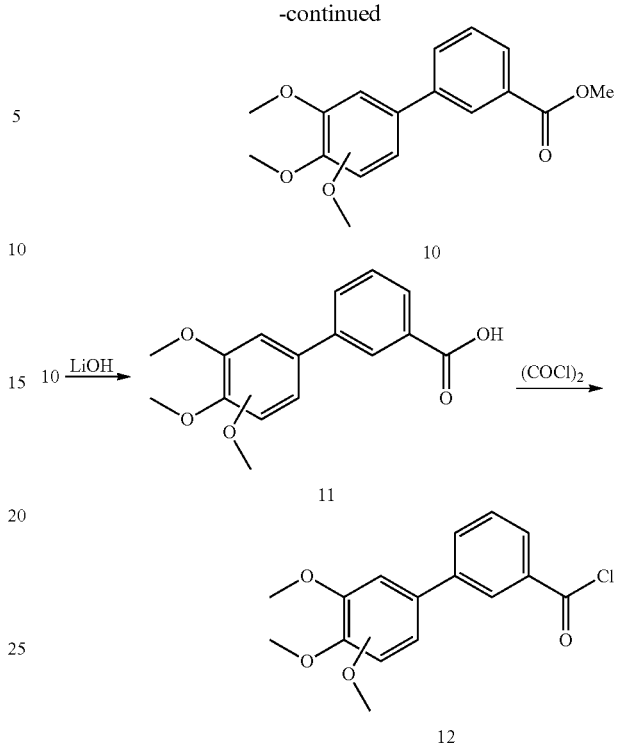

In SCHEME 2 a carboxy substituted thiophene like (4) is reacted to the corresponding ethyl ester (5) under heating in acidic ethanol. Ester (5) is brominated with N-bromosuccinimide in anhydrous chloroform and glacial acetic acid to give (6) which is further reacted with 2-Amino-benzeneboronic acid under a state-of-the-art Suzuki transformation (i.e. Tetrakis(triphenylphosphine)-palladium, aqueous sodium carbonate, ethanol, toluene) to the biaryl (7). Biaryl (7) is reacted with a trimethoxy-phenyl-alkylic acid, EDC, triethylamine and DMAP in a chlorinated solvent to the amide (8). Alternatively DIC and HOBt may be used for this reaction step.

SCHEME 3

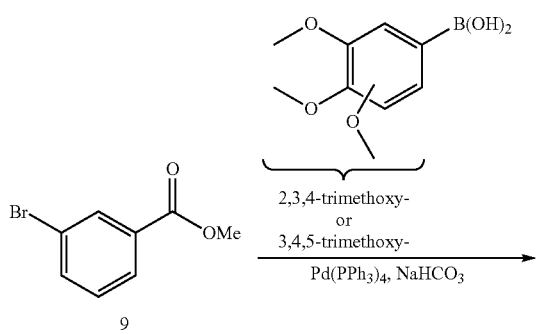

In SCHEME 3 Methyl-3-bromobenzoate (9) is reacted under inert conditions with a Trimethoxyphenylboronic acid under Suzuki-type basic conditions (Pd(PPh$_3$)$_4$ and aqueous sodium bicarbonate in dimethoxyethane) to a biphenyl of type (10) which is further hydrolized with aqueous lithium hydroxide in acetonitrile to give the corresponding carboxylic acid (11) which was converted to building block of type (12) by reaction with oxalyl chloride in anhydrous dichloromethane.

SCHEME 4

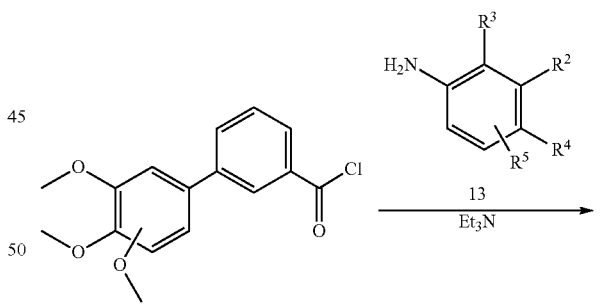

In SCHEME 4 an acid chloride like (12) is reacted with an aniline of general type (13) under basic conditions (triethylamine in a chlorinated solvent) to form the anilide (14). Alternatively pyridine may be used for this reaction step.

In case that $R^2$ and/or $R^4$ contain carboxylic acid functionalities, those are protected as their corresponding methyl or ethyl esters before and hydrolized afterwards to release the carboxylic acid functionalities. The ester hydrolysis is done with LiOH in MeCN or THF/MeOH.

The synthesis sequence shown in SCHEME 4 leading to compounds like (14) is not only reduced to X—Y—H and Y—H building blocks like (13) but may be generally applied to all other X—Y—H and Y—H type building blocks leading to compounds of type (A1), (A2), (B1) and (B2) as shown in the paragraphs before.

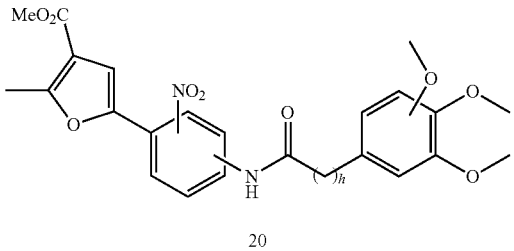

20

SCHEME 5

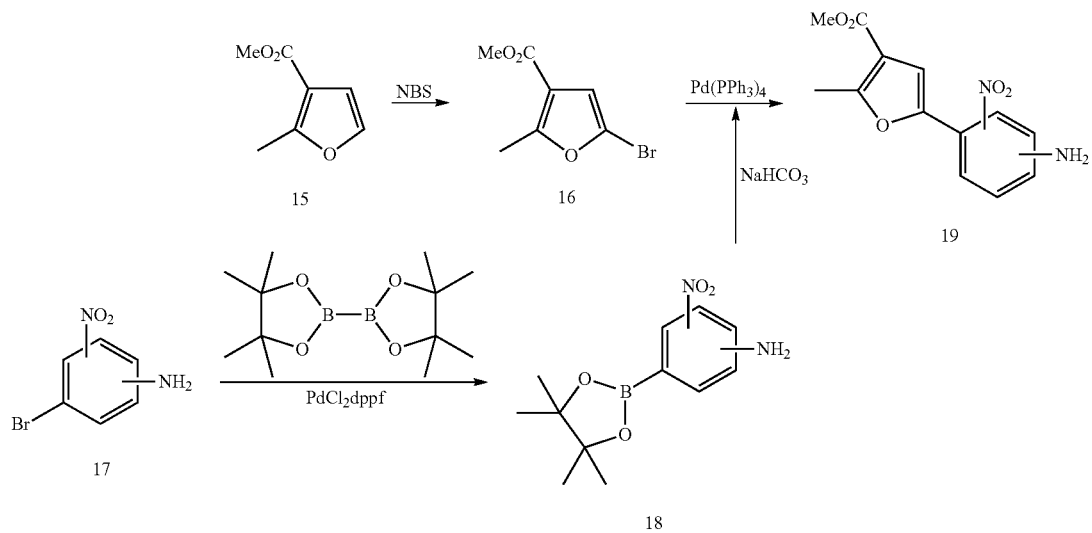

In SCHEME 5 the generation of building block (19) is outlined, whereby the furan (16) is available by NBS-bromination of methyl furoate (15) and pinacolyl borane of type (18) is available by Pd-catalyzed boration of anilines like (17). Suzuki-type coupling of (16) and (18) with Pd(PPh$_3$)$_4$ leads to biaryls of type (19).

SCHEME 6

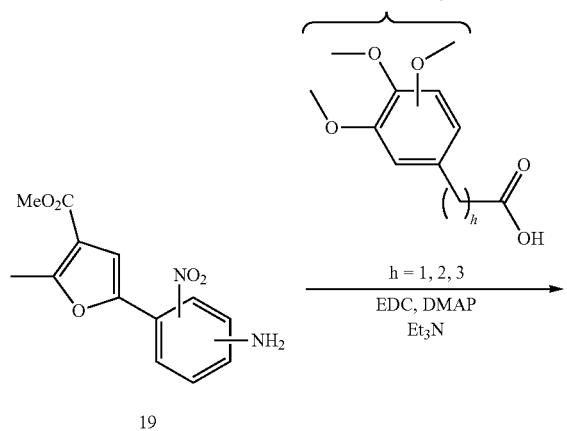

-continued

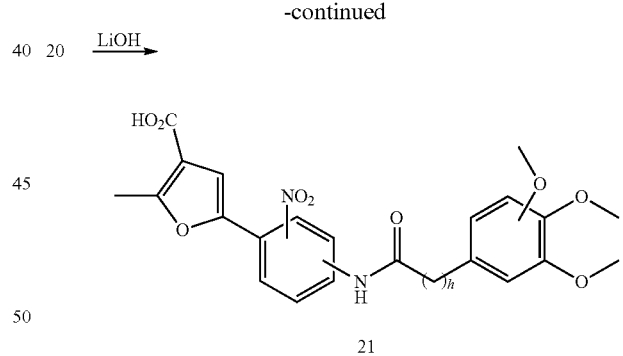

21

In SCHEME 6 a biaryl of type (19) is reacted with a trimethoxy-phenyl-alkylic acid under state-of-the-art conditions (i.e. N'-(3-dimethylaminopropyl)-N-ethyl carbodiimide (EDC), triethylamine and 4-dimethylaminopyridine (DMAP) in a chlorinated solvent) to the amide of type (20). Alternatively diisopropyl carbodiimide (DIC) and hydroxybenzotriazole (HOBt) may be used for this reaction step. (20) is then hydrolized to acid of type (21) whether with LiOH in MeCN or THF/MeOH.

The present invention is furthermore illustrated by the following representative examples.

EXAMPLE 1

{3-[3-(2,3,4-Trimethoxy-phenyl)-propionylamino]-phenyl}-acetic acid methyl ester (24)

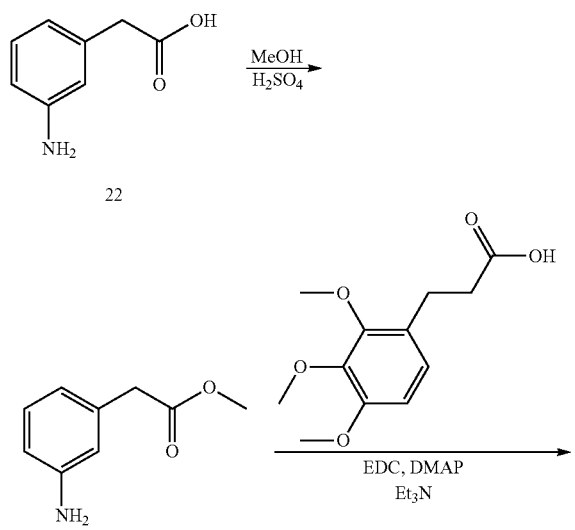

Step 1:

Dissolve (3-Amino-phenyl)-acetic acid ((22), 700 mg, 4.63 mmol) in MeOH (21 mL) and add conc. sulfuric acid (0.27 mL, 5.09 mmol). Stir the reaction mixture for 2 d under reflux. Cooled mixture to room temperature (rt), remove solvent under reduced pressure and prepurify the residue by flushing it over a short pad of silica gel using EtOAc. Remove solvent again and partition the residue between EtOAc and saturated aqu. NaHCO₃ (1+1). Extracte the aqueous layer 3 times with EtOAc, washe the combined organic layers with brine and dried with Na₂SO₄. Remove solvent under reduced pressure and dry the residue without further purification in oil pump vacuum to obtain product (23) as a light yellow oil (708 mg, 92%). NMR (400 MHz, CDCl₃): 3.51 (s, 2H); 3.67 (s, 3 H); 6.57 (dd, 1H, J₁=7.8 Hz, J₂=1.8 Hz); 6.60 (br.Ψt, 1H, J=1.8 Hz); 6.65 (br.d, 1H, J≈7.8 Hz); 7.08 (Ψt, 1H, J=7.8 Hz).

Step 2:

(The following reaction is done in an anhydrous N₂ atmosphere.) Dissolve EDC hydrochloride (187 mg, 0.98 mmol) and triethylamine (0.14 mL, 1.00 mmol) in anhydrous dichloromethane (3.5 mL) and stir for 5 min at rt. Added 3-(2,3,4-Trimethoxy-phenyl)-propionic acid (234 mg, 0.97 mmol) and DMAP (12 mg, 0.10 mmol) and stir for 10 min. Add ester (23) (107 mg, 0.65 mmol) and stir the reaction solution overnight at rt.

Hydrolize the reaction solution with saturated aqu. NH₄Cl followed by water, separate layers, extracte aqu. layer with dichloromethane (3 times) and washe the combined organic layers with water and brine and dry with Na₂SO₄. Remove solvent under reduced pressure.

Purify crude product by preparative radial chromatography (silica gel 60PF, EtOAc/CyH 1+1) to obtain product (24) as a white solid (209 mg, 83%). [K. C. Nicolaou; P. S. Baran; Y.-L. Thong; K. Sugita; *J. Am. Chem. Soc.;* 2002; 124; 10; 2212-2220]. ¹H NMR (400 MHz, CDCl₃): 2.62 (t, 2H, J=7.5 Hz); 2.95 (t, 2H, J=7.5 Hz); 3.58 (s, 2H); 3.67 (s, 3H); 3.82 (s, 3H); 3.84 (s, 3H); 3.91 (s, 3H); 6.59 (d, 1H, J=8.6 Hz); 6.86 (d, 1H, J=8.6 Hz); 6.98 (br.d, 1H, J=7.8 Hz); 7.32 (Ψt, 1H, J=7.8 Hz); 7.38 (br.d, 1H, J=7.8 Hz); 7.41 (br.s, 1H).

EXAMPLE 2

(5-{2-[2-(2,3,4-Trimethoxyphenyl)-acetylamino]-phenyl}-thiophen-2-yl]acetic acid (31)

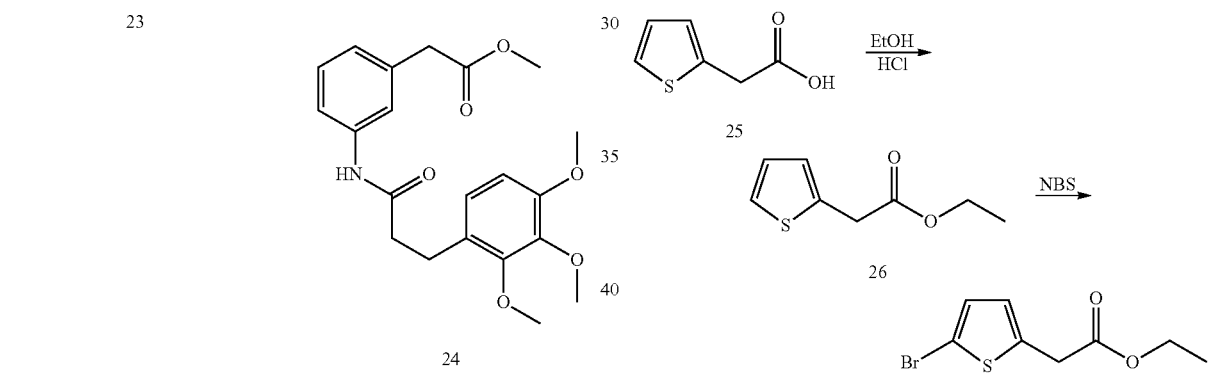

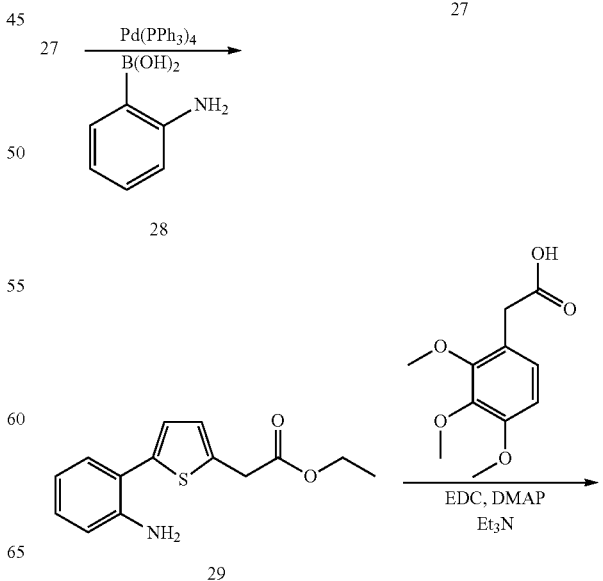

-continued

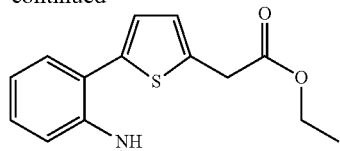

30

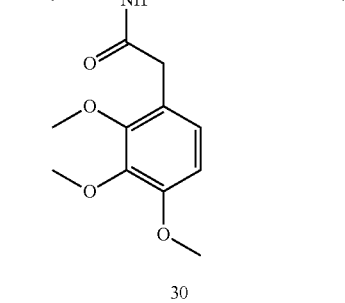

30 →LiOH

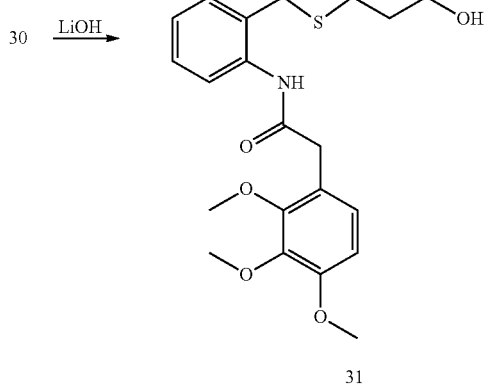

31

Step 1:

Dissolve Thiophene-2-yl-acetic acid (25) (2.44 g, 17.1 mmol) in ethanol (35 mL) and add fuming aqu. hydrochloric acid (few drops). Stir the reaction mixture for 19 h at 70° C. Cool mixture to rt, remove solvent under reduced pressure and resolve the residue in EtOAc. Wash this organic layer 3 times with 5% aqu. $Na_2CO_3$ and extract the combined aqueous layer 3 times with EtOAc. Wash the combined organic layers with brine and dry with $Na_2SO_4$. Remove solvent under reduced pressure and dry the residue without further purification in oil pump vacuum to obtain product (26) as a light brown oil (2.78 g, 95%). [J. Kunes; V. Balsanek; M. Pour; V. Buchta; *Collect. Czech. Chem. Commun.*, 2001, 66; 12; 1809-1830]. NMR (400 MHz, $CDCl_3$): 1.26 (t, 3H, J=7.1 Hz); 3.81 (s, 2 H); 4.17 (q, 2H, J=7.1 Hz); 6.91-6.96 (m, 2H); 7.20 (d, 1H, J=4.8 Hz).

Step 2:

(The following reaction is done in an anhydrous $N_2$ atmosphere.) Dissolve ester (26) (1.30 g, 7.64 mmol) in anhydrous chloroform (6.0 mL) and glacial acetic acid (6.0 mL), add N-Bromosuccinimide (1.39 g, 7.79 mmol) in portions and stir the mixture for 23 h at rt. The mixture is diluted with an equal volume of water, the organic layer separated and washed with a 1M aqu. NaOH, water, again with 1M aqu. NaOH and water (2 times). Finally wash the organic layer with brine and dry with $Na_2SO_4$. Remove solvent under reduced pressure. Purify crude product by preparative radial chromatography (silica gel 60PF, CyH/EtOAc 5+1] to obtain product (27) as an impured (according to NMR: 20% sideproduct) orange liquid (1.61 g, 85%) which is used without any further purification.

[P. M. Jackson; C. J. Moody; P. Sha; *J. Chem. Soc. Perkin Trans. 1*; 1990; 2909-2918]. $^1$H NMR (400 MHz, $CDCl_3$): 1.26 (t, 3H, J=7.1 Hz); 3.73 (s, 2H); 4.17 (q, 2H, J=7.1 Hz); 6.67 (d, 1H, J=3.5 Hz); 6.88 (d, 1H, J=3.5 Hz).

Step 3:

(The following reaction is done in an oxygenfree $N_2$ atmosphere.) Ethanol (1.47 mL), Tetrakis-(triphenylphosphine)-palladium(0) (59.0 mg, 2.5 mol %) and aqu. $Na_2CO_3$ (1.60 g, 5.60 mmol; presolved in 2.0 mL $H_2O$) are subsequently added to dissolved 2-Amino-benzeneboronic acid (28) (341 mg, 2.20 mmol) in toluene (16 mL). The reaction mixture is degassed 5 times and flooded with $N_2$ again. Add bromide (27) (498 mg, 2.00 mmol) and rinse with toluene (4.5 mL), degas again (5 times) and stir the reaction solution 21 h at 100° C. Partition the reaction solution between EtOAc and brine (1+1) and extract the separated aqueous layer 3 times with EtOAc. Wash combined organic layer with brine and dry with $Na_2SO_4$. Remove solvent under reduced pressure and purify the crude product by preparative radial chromatography (silica gel 60PF, CyH/EtOAc 6+1, later 3+1] to obtain product (29) as a light yellow solid (300 mg, 57%). [N. Miyaura; A. Suzuki; *Chem. Rev.*; 1995; 95; 2457]. $^1$H NMR (400 MHz, $CDCl_3$): 1.28 (t, 3H, J=7.1 Hz); 3.82 (s, 2H); 4.19 (q, 2H, J=7.1 Hz); 6.77-6.84 (m, 2H); 6.91 (d, 1H, J=3.5 Hz); 7.04 (d, 1H, J=3.5 Hz); 7.13 (td, 1H, J=7.8 Hz, 1.3 Hz); 7.25 (d, 1H, J=7.8 Hz).

Step 4:

(The following reaction is done in an anhydrous $N_2$ atmosphere.) Suspend EDC hydrochloride (86.3 mg, 0.45 mmol) in anhydrous dichloromethane (1.4 mL), add triethylamine (0.063 mL, 0.45 mmol) and stir for 10 min at rt. Add 2-(2,3,4-Trimethoxy-phenyl)-acetic acid (74.7 mg, 0.33 mmol) and DMAP (3.7 mg, 0.03 mmol) and stir for 15 min. Added ester (29) (64.9 mg, 0.30 mmol) and stir the reaction solution 22 h at rt. Partition the reaction solution between dichloromethane and water (1+1), separate layers and extract aqu. layer with dichloromethane (3 times). Wash the combined organic layer with brine and dry with $Na_2SO_4$. Purify crude product by preparative radial chromatography (silica gel 60PF, CyH/EtOAc 3+2) to obtain product (30) as yellow oil (118 mg, 84%). $^1$H NMR (400 MHz, $CDCl_3$): 1.29 (t, 3H, J=7.1 Hz); 3.58 (s, 2H); 3.74 (s, 3H); 3.78 (s, 3H); 3.79-3.80 (m, 2H); 3.86 (s, 2H); 4.20 (q, 2H, J=7.1 Hz); 6.58 (d, 1H, J=8.6 Hz); 6.59 (d, 1H, J=3.5 Hz); 6.75 (d, 1H, J=3.5 Hz); 6.85 (d, 1H, J=8.6 Hz); 7.05 (t, 1H, J=7.8 Hz); 7.26 (dd, 1H, J=7.8 Hz, 1.3 Hz); 7.30 (td, 1H, J=7.8 Hz, 1.3 Hz); 7.90 (br.s; 1H), 8.38 (d, 1H, J=8.3 Hz).

Step 5:

Dissolve ester (30) (118 mg, 0.25 mmol) in methanol (8.0 mL), add a 1M aqu. LiOH solution (1.76 mL, 1.76 mmol) and stir 20 h at rt. Remove solvent under reduced pressure and partition residue between $CHCl_3$ and 0.5 M HCl (1+1). Separate the aqueous layer and extract 3 times with $CHCl_3$. Wash the combined organic layer with brine and dry with $Na_2SO_4$. Remove solvent under reduced pressure and dry the residue without further purification in oil pump vacuum to obtain crude product (31) as light brown foam (120 mg, quant.). NMR (400 MHz, $CDCl_3$): 3.58 (s, 2H); 3.73 (s, 3H); 3.78 (s, 3H); 3.85 (s, 2 H); 3.86 (s, 3H); 6.58-6.61 (m, 1H); 6.59 (d, 1H, J=8.3 Hz); 6.77 (d, 1H, J=3.5 Hz); 6.86 (d, 1H, J=8.3 Hz); 7.06 (t, 1H, J=7.8 Hz); 7.22-7.27 (m, 1H); 7.31 (td, 1H, J=7.8 Hz, 1.3 Hz); 7.86 (br.s, 1H); 8.37 (d, 1H, J=8.3 Hz).

EXAMPLE 3

(5-{2-[(2',3',4'-Trimethoxy-biphenyl-3-carbonyl)-amino]-phenyl}-thiophen-2-yl)-acetic acid methyl ester (37)

SCHEME 9

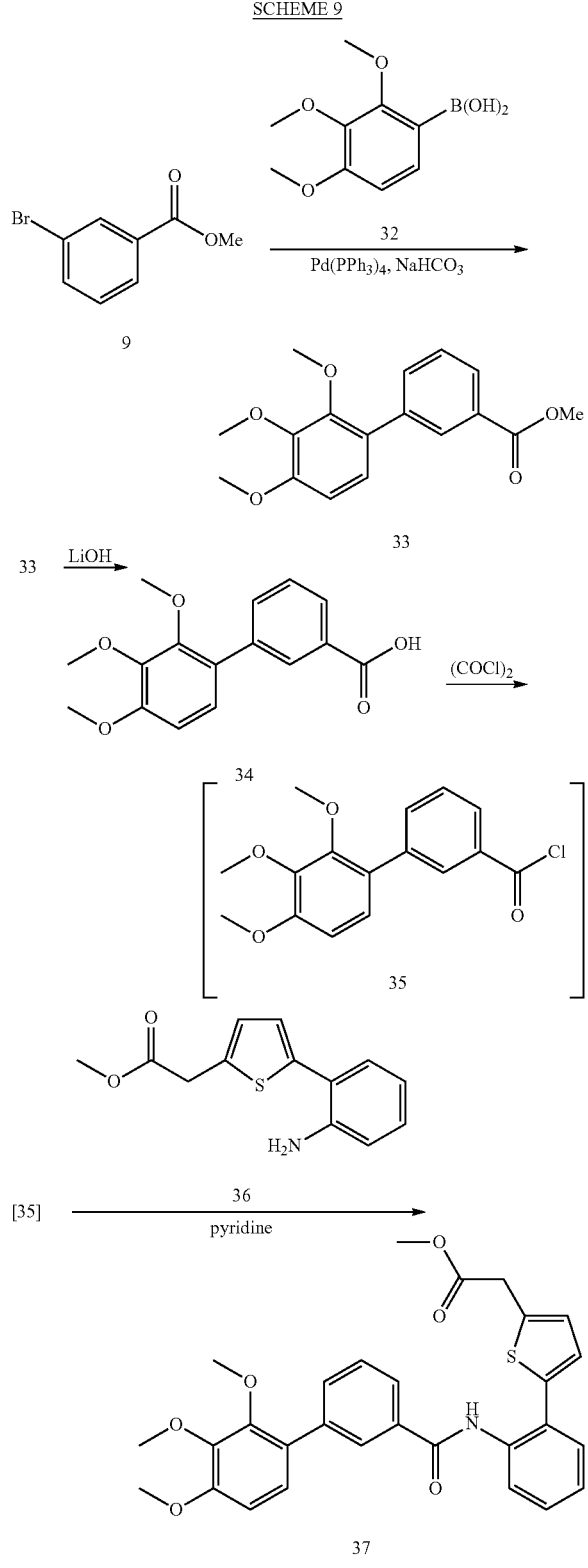

Step 1:

(The following reaction is done in an $N_2$ atmosphere.) To a solution of 2,3,4-Trimethoxyphenylboronic acid (32) (1.40 g, 6.60 mmol) in toluene (15.0 mL) is added EtOH (2.0 mL), Pd(PPh$_3$)$_4$ (208 mg, 0.18 mmol) and Na$_2$CO$_3$.10 H$_2$O (4.81 g, 16.80 mmol) in water (5.2 mL). The resulting mixture is carefully degassed (5 times alternating vacuum and flushing with N$_2$). A solution of Methyl-3-bromobenzoate (9) (1.29 g, 6.00 mmol) in toluene (9.0 mL) is added by syringe, the resulting mixture is again carefully degassed and stirred overnight at 100° C. Partition the mixture between brine/EtOAc (1+1), separate layers, extract the aqu. layer with EtOAc (3×), wash the combined organic layer with brine, dry with Na$_2$SO$_4$ and remove solvent. Purify crude product by preparative radial chromatography (silica gel, EtOAc/CyH 1+5) to obtain 2',3',4'-Trimethoxy-biphenyl-3-carboxylic acid methyl ester (33) as a yellowish oil (1.07 g, 58%). $^1$H NMR (400 MHz, CDCl$_3$): 3.66 (s, 3H); 3.89 (s, 3H); 3.92 (s, 6H); 6.74 (d, 1H, J=8.6 Hz); 7.03 (d, 1H, J=8.6 Hz); 7.44 (t, 1H, J=7.8 Hz); 7.70 (d, 1H, J=7.6 Hz); 7.97 (d, 1H, J=7.8 Hz); 8.15 (br.s 1H).

Step 2:

Dissolve 2',3',4'-Trimethoxy-biphenyl-3-carboxylic acid methyl ester (33) (566 mg, 1.87 mmol) in MeCN (19.0 mL) at rt and add 1M aqu LiOH (9.36 mL, 9.36 mmol). Stir reaction mixture overnight at rt. Quench reaction mixture (cooling bath) with 1M aqu. HCl (to get pH ca. 3). Extract the mixture with EtOAc (3×), wash the combined organic layer with brine and dry with Na$_2$SO$_4$. Recrystallize crude product from EtOAc/CyH 1+3 to obtain 2',3',4'-Trimethoxy-biphenyl-3-carboxylic acid (34) as a white solid (392 mg, 72%). $^1$H NMR (400 MHz, CD$_3$OD: 3.68 (s, 3H); 3.93 (br.s, 6H); 6.92 (d, 1H, J=8.6 Hz); 7.11 (d, 1H, J=8.6 Hz); 7.54 (t, 1H, J=7.7 Hz); 7.75 (d, 1H, J=7.6 Hz); 8.01 (d, 1H, J=7.8 Hz); 8.18 (br.s 1H).

Step 3:

(The following reaction is done in an anhydrous $N_2$ atmosphere.) Dissolve 2',3',4'-Trimethoxy-biphenyl-3-carboxylic acid (34) (107 mg, 0.37 mmol) in anhydrous DCM (3.0 mL) and add anhydrous DMF (3 drops, cat. amount). Then add slowly oxalyl chloride (424, 0.48 mmol) by keeping temperature at ca. 15° C. with a water bath and stir the turbid mixture for additional 2 h at rt. Transfer the formed crude solution of 2',3',4'-Trimethoxy-biphenyl-3-carbonyl chloride (35) to an ice cooled solution of [5-(2-Amino-phenyl)-thiophen-2-yl]-acetic acid methyl ester (36) (70 mg, 0.28 mmol) in anhydrous DCM (4.5 mL) and anhydrous pyridine (0.75 mL). Stir the reaction mixture for 3 h at rt. Pour the reaction mixture into ice cooled 1M aqu. HCl, extract with DCM (3×), wash the combined organic layer with brine and dry with Na$_2$SO$_4$. Purify the crude product by preparative radial chromatography (silica gel, EtOAc/CyH 1+3, later 1+2) to obtain (5-{2-(2-[(2',3',4'-Trimethoxy-biphenyl-3-carbonyl)-amino]-phenyl}-thiophen-2-yl)-acetic acid methyl ester (37) as a brownish sticky solid (96 mg, 65%). $^1$H NMR (400 MHz, CDCl$_3$): 3.64 (s, 3H); 3.71 (s, 3H); 3.84 (s, 2H); 3.90 (s, 3H); 3.92 (s, 3H); 6.75 (d, 1H, J=8.8 Hz); 6.97 (d, 1H, J=3.5 Hz); 7.01 (d, 1H, J=8.8 Hz); 7.03 (d, 1H, J=3.5 Hz); 7.16 (br.t, 1H, J=7.6 Hz); 7.36-7.43 (m, 2H); 7.46 (t, 1H, J=7.7 Hz); 7.67 (Ψdd, 2H, J$_1$=7.6 Hz, J$_2$=1.5 Hz); 7.91 (br.s 1H); 8.41 (br.s 1H); 8.50 (d, 1H, J=8.6 Hz).

EXAMPLE 4

5-{2-Amino-4-[2-(3,4,5-trimethoxy-phenyl)-acetylamino]-phenyl}-2-methyl-furan-3-carboxylic acid (42)

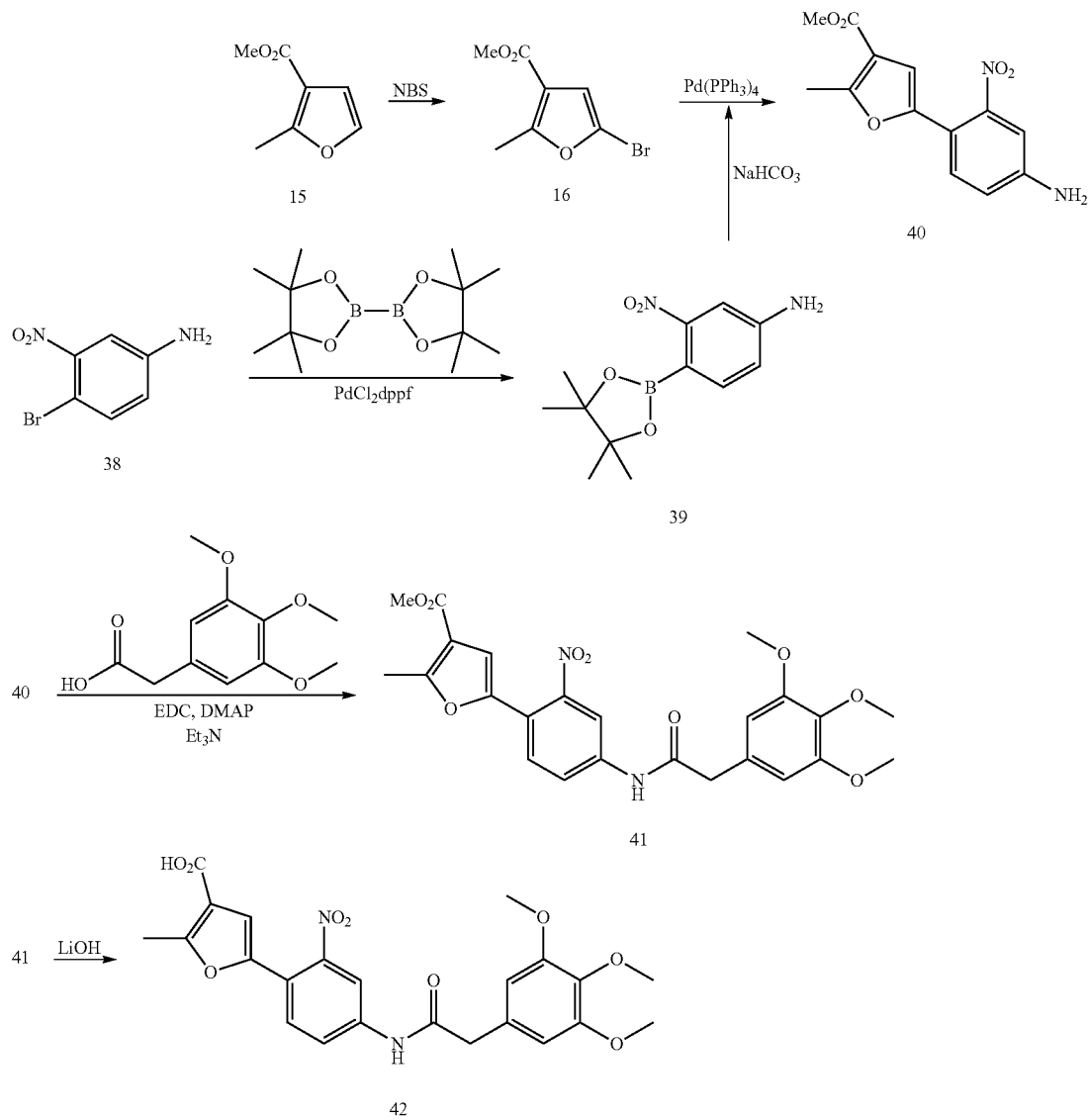

SCHEME 10

Step 1:

(The following reaction is done under exclusion of light.) Dissolve 2-Methyl-furan-3-carboxylic acid methyl ester (15) (2.00 mL, 15.9 mmol) in chloroform (11 mL) and glacial acetic acid (11 mL) and add NBS (3.85 g, 21.6 mmol) portionwise in between a period of 75 min. Stir the reaction suspension for additional 16 h at rt. Add water to the reaction mixture and extract the aqu. layer with DCM (2 times), wash the combined organic layer with 2 M aqu. NaOH, water and brine and dry it with $Na_2SO_4$ to obtain 5-Bromo-2-methyl-furan-3-carboxylic acid methyl ester (16) (2.80 g, 80%) as a red brown oil. No further purification. $^1$H NMR (400 MHz, $CDCl_3$): 2.54 (s, 3H); 3.80 (s, 3H); 6.53 (s, 1H).

Step 2:

(The following reaction is done in a $N_2$ atmosphere.) Dissolve $PdCl_2$(dppf) $CH_2Cl_2$ (245 mg, 0.30 mmol), KOAc (2.52 g, 25.7 mmol) and Bis-(pinacolato)diboron (3.81 g, 15.00 mmol) in anhydrous DMSO (50 mL) and add 4-Bromo-3-nitro-phenylamine (38) (2.17 g, 10.00 mmol). Degas the mixture carefully and flush with $N_2$ again (5 times) and stir it for 24 h at 80° C. Cool the reaction mixture to rt and partition it between water and toluene. Extract the aqu. layer with EtOAc (3 times), wash the combined organic layer with water and brine and dry it with $Na_2SO_4$. The obtained crude residue is filtrated through a short pad of silica gel using EtOAc/CyH (1+1) to obtain 3-Nitro-4-(4,4,5,5-tetramethyl-[1,3,2]dioxaborolan-2-yl)-phenylamine (39) (2.04 g, 77%) as a dark red solid. No further purification. $^1$H NMR (400 MHz, $CDCl_3$): 1.37 (s, 12H); 3.95 (br.s, 2H); 6.87 (dd, 1H, $J_1$=7.8 Hz; $J_2$=7.30 (d, 1H, J=8.1 Hz); 7.35 (d, 1H, J=2.3 Hz).

Step 3:

(The following reaction is done in a N$_2$ atmosphere.) Dissolve Pd(PPh$_3$)$_4$ (59 mg, 0.05 mmol) and 5-Bromo-2-methyl-furan-3-carboxylic acid methyl ester (23) (447 mg, 2.04 mmol) in DME (3 mL) and stir for 10 min at rt. Add 3-Nitro-4-(4,4,5,5-tetramethyl-[1,3,2]dioxaborolan-2-yl)-phenylamine (39) (465 mg, 1.76 mmol) followed by an aqu. 1M sodium bicarbonate solution (5.10 mL, 5.10 mmol). Degas the reaction mixture carefully, flush with N$_2$ (5 times) and stir for 4.5 h at 90° C. (reflux). Cool reaction mixture to rt, remove organic solvent under reduced pressure and partition the residue between water and EtOAc. Extract the aqu. layer with EtOAc (3 times), wash the combined organic layer with water and brine and dry it with Na$_2$SO$_4$. Purify the obtained crude product by flash chromatography (silica gel, EtOAc/CyH 1+3, later 1+2) to obtain 5-(4-Amino-2-nitro-phenyl)-2-methyl-furan-3-carboxylic acid methyl ester (40) (167 mg, 34%) as a red solid. $^1$H NMR (400 MHz, CDCl$_3$): 2.57 (s, 3H); 3.81 (s, 3H); 4.05 (br.s, 2H); 6.68 (s, 1H); 6.81 (dd, 1H, J$_1$=8.3 Hz, J$_2$=2.3 Hz); 6.99 (d, 1H, J=2.3 Hz); 7.39 (d, 1H, J=8.3 Hz).

Step 4:

(The following reaction is done in an anhydrous N$_2$ atmosphere.) Suspend EDC HCl (138 mg, 0.72 mmol) and Et$_3$N (101 µL, 0.72) in anhydrous DCM (4.5 mL) and stir the resulting solution for 5 min at rt. Add 2-(3,4,5-Trimethoxy-phenyl)-acetic acid (163 mg, 0.72 mmol) and DMAP (8 mg, 0.07 mmol) and stir the resulting solution for 10 min. Add 5-(4-Amino-2-nitro-phenyl)-2-methyl-furan-3-carboxylic acid methyl ester (40) (100 mg, to 0.36 mmol) and stir the reaction solution for 22 h at rt. Quench reaction solution with sat. aqu. NH$_4$Cl and water, separate layers and extract aqu. layer with DCM (3 times). Wash the combined organic layer with water and brine and dry with Na$_2$SO$_4$. Purify the crude product by preparative radial chromatography (silica gel, EtOAc/CyH 1+1) to obtain 2-Methyl-5-{2-nitro-4-[2-(3,4,5-trimethoxy-phenyl)-acetylamino]-phenyl}-furan-3-carboxylic acid methyl ester (41) (96 mg, 55%) as an yellow solid. $^1$H NMR (400 MHz, CDCl$_3$): 2.55 (s, 3H); 3.65 (s, 2H); 3.79 (s, 3H); 3.81 (s, 6H); 3.82 (s, 3H); 6.50 (s, 2H); 6.77 (s, 1H); 7.53 (d, 1H, J=8.6 Hz); 7.66 (dd, 1H, J$_1$=8.6 Hz, J$_2$=2.0 Hz); 7.93 (br.s, 1H); 7.96 (d, 1H, J=2.0 Hz).

Step 5:

Dissolve 2-Methyl-5-{2-nitro-4-[2-(3,4,5-trimethoxy-phenyl)-acetylamino]-phenyl}-furan-3-carboxylic acid methyl ester (41) (50 mg, 0.10 mmol) in THF (1.0 mL) and MeOH (0.5 mL) at rt and add 1M aqu LiOH (525 µL, 0.52 mmol). Stir the reaction mixture for 17 h at rt. Add dropwise 1M aqu. HCl (580 µL, 0.58 mmol) and extract the mixture with EtOAc (3 times), wash the combined organic layer with brine and dry it with Na$_2$SO$_4$. Purify the obtained crude product by preparative TLC (silica gel, EtOAc/MeOH 9+1) to obtain 2-Methyl-5-(2-nitro-4-[2-(3,4,5-trimethoxy-phenyl)-acetylamino]-phenyl)-furan-3-carboxylic acid (42) (35 mg, 71%) as a brown sticky solid. $^1$H NMR (400 MHz, CDCl$_3$): 2.61 (s, 3H); 3.70 (s, 2H); 3.86 (s, 3H); 3.87 (s, 6H); 6.51 (s, 2H); 6.85 (s, 1H); 7.29 (br.s, 1H); 7.58 (d, 1H, J=8.6 Hz); 7.62 (dd, 1H, J$_1$=9.0 Hz, J$_2$=2.2 Hz); 7.98 (d, 1H, J=2.0 Hz).

EXAMPLE 5

{4-[2-(3,4,5-Trimethoxy-phenyl)-acetyl]-piperazin-1-yl}-acetic acid ethyl ester (44)

SCHEME 11

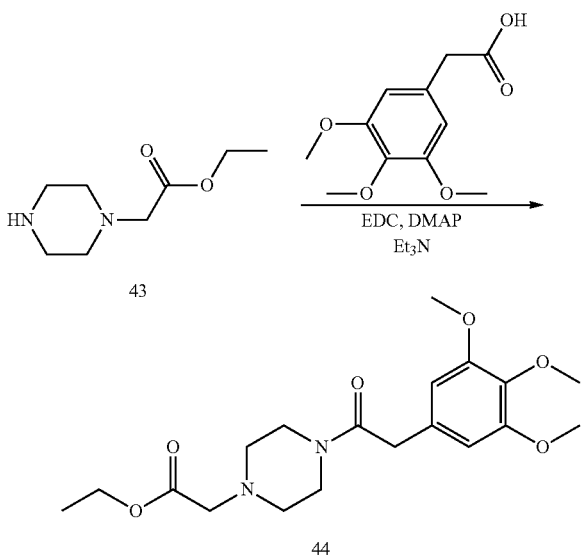

(The following reaction is done in an anhydrous N$_2$ atmosphere.) Suspend EDC HCl (188 mg, 0.98 mmol) and Et$_3$N (137 µL, 0.98 mmol) in anhydrous DCM (1.0 mL) and stir the resulting solution for 5 min at rt. Add 2-(3,4,5-Trimethoxy-phenyl)-acetic acid (163 mg, 0.72 mmol) and DMAP (8 mg, 0.07 mmol) and stir the resulting solution for 10 min. Add 1-(Ethoxycarbonylmethyl)piperazine (43) (112 mg, 0.65 mmol) and stir the reaction solution overnight at rt. Quench reaction solution with sat. aqu. NH$_4$Cl and water, separate layers and extract aqu. layer with DCM (3 times). Wash the combined organic layer with water and brine and dry with Na$_2$SO$_4$. Purify the crude product by preparative radial chromatography (silica gel, EtOAc/MeOH 10+1) to obtain {4-[2-(3,4,5-Trimethoxy-phenyl)-acetyl]-piperazin-1-yl}-acetic acid ethyl ester (44) (99 mg, 40%) as a colorless oil. $^1$H NMR (400 MHz, CDCl$_3$): 1.25 (t, 3H, J=7.1 Hz); 2.48 (br.m, 2H); 2.58 (br.m, 2H); 3.21 (br.s, 2H); 3.53 (br.m, 2H); 3.65 (s, 2H); 3.71 (br.m, 2H); 3.81 (s, 3H); 3.82 (s, 6H); 4.16 (q, 2H, J=7.1 Hz); 6.42 (s, 2H).

EXAMPLE 6

{4-[3-(3,4,5-Trimethoxy-phenyl)-propionyl]-piperazin-1-yl}-acetic acid (46)

SCHEME 12

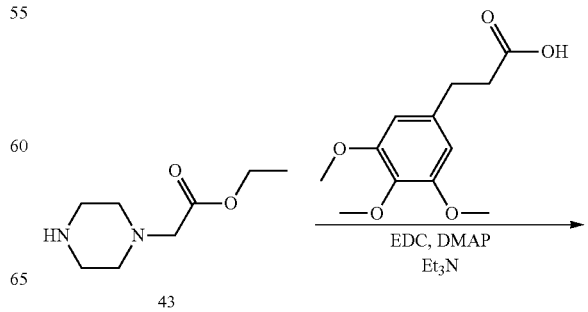

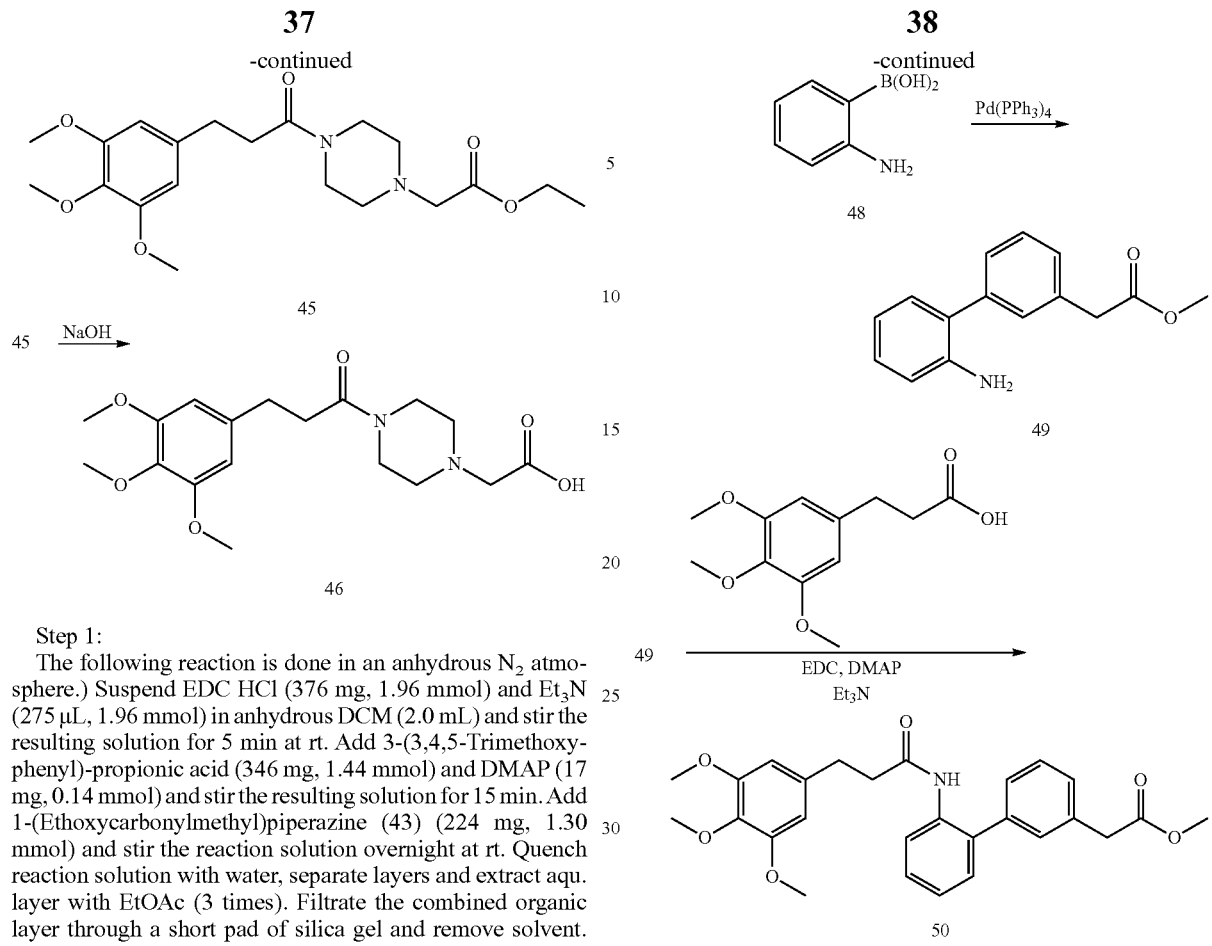

Step 1:

The following reaction is done in an anhydrous N₂ atmosphere.) Suspend EDC HCl (376 mg, 1.96 mmol) and Et₃N (275 µL, 1.96 mmol) in anhydrous DCM (2.0 mL) and stir the resulting solution for 5 min at rt. Add 3-(3,4,5-Trimethoxyphenyl)-propionic acid (346 mg, 1.44 mmol) and DMAP (17 mg, 0.14 mmol) and stir the resulting solution for 15 min. Add 1-(Ethoxycarbonylmethyl)piperazine (43) (224 mg, 1.30 mmol) and stir the reaction solution overnight at rt. Quench reaction solution with water, separate layers and extract aqu. layer with EtOAc (3 times). Filtrate the combined organic layer through a short pad of silica gel and remove solvent. Purify the crude product by preparative radial chromatography (silica gel, EtOAc/MeOH 9+1) to obtain {4-[3-(3,4,5-Trimethoxy-phenyl)-propionyl]-piperazin-1-yl}-acetic acid ethyl ester (45) (426 mg, 83%) as a colorless oil. $^1$H NMR (400 MHz, CDCl₃): 1.26 (t, 3H, J=7.1 Hz); 2.45-2.70 (br.m, 6H); 2.89 (t, 2H, J=7.7 Hz); 3.26 (br.s, 2H); 3.43-3.56 (br.m, 2H); 3.61-3.76 (br.m, 2H); 3.80 (s, 3H); 3.83 (s, 6H); 4.18 (q, 2H, J=7.1 Hz); 6.41 (s, 2H).

Step 2:

Dissolve {4-[3-(3,4,5-Trimethoxy-phenyl)-propionyl]-piperazin-1-yl}-acetic acid ethyl ester (45) (100 mg, 0.25 mmol) in MeOH (2.0 mL) at rt and add 2M aqu NaOH (260 µL, 0.52 mmol). Stir the reaction mixture for 1 h under reflux. Add dropwise 1M aqu. HCl (550 µL, 0.55 mmol), extract the mixture with EtOAc (3 times) and remove solvent obtain {4-[3-(3,4,5-Trimethoxy-phenyl)-propionyl]-piperazin-1-yl}-acetic acid (46) (88 mg, 95%) as a brown sticky solid. No further purification. $^1$H NMR (400 MHz, CDCl₃/CD₃OD 9+1): 2.54 (br.t, 2H); 2.78 (t, 2H, J=7.5 Hz); 2.83-3.10 (br.m, 2H); 3.24 (s, 2H); 3.43-3.62 (br.m, 2H); 3.68 (s, 3H); 3.73 (s, 6H); 3.74-3.85 (br.m, 4H); 6.34 (s, 2H).

EXAMPLE 7

{2'-[3-(3,4,5-Trimethoxy-phenyl)-propionylamino]-biphenyl-3-yl}-acetic acid methyl ester (50)

SCHEME 13

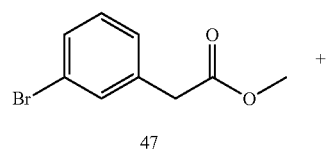

47

Step 1:

(The following reaction is done in an oxygenfree N₂ atmosphere.) Add ethanol (0.8 mL), Tetrakis-(triphenylphosphine)-palladium(0) (30 mg, 2.2 mol %) and Na₂CO₃ decahydrate (944 mg, 3.30 mmol; presolved in 1.2 mL H₂O) subsequently to dissolved 2-Amino-benzeneboronic acid (48) (201 mg, 1.30 mmol) in toluene (6.0 mL). Degas the reaction mixture for 5 times and flood with N₂ again. Add (3-Bromo-phenyl)-acetic acid methyl ester (47) (270 mg, 1.18 mmol) in toluene (6.0 mL), degas again (5 times) and stir the reaction solution overnight at 100° C. Partition the reaction solution between EtOAc and brine (1+1) and extract the separated aqueous layer 3 times with EtOAc. Wash combined organic layer with brine and dry with Na₂SO₄. Remove solvent under reduced pressure and purify the crude product by preparative radial chromatography (silica gel 60PF, CyH/EtOAc 3+1) to obtain (2'-Amino-biphenyl-3-yl)-acetic acid methyl ester (49) as an orange oil (304 mg, 81%). $^1$H NMR (400 MHz, CDCl₃): 3.66 (s, 2H); 3.69 (s, 3H); 3.62-3.86 (br.s, 2H); 6.75 (d, 1H, J=8.1 Hz); 6.80 (t, 1H, J=7.3 Hz); 7.11 (d, 1H, J=7.3 Hz); 7.15 (d, 1H, J=8.1 Hz); 7.22-7.26 (br.m, 1H); 7.32-7.42 (m, 3H).

Step 2:

(The following reaction is done in an anhydrous N₂ atmosphere.) Suspend EDC HCl (61 mg, 0.32 mmol) and Et₃N (44 µL, 0.32 mmol) in anhydrous DCM (1.0 mL) and stir the resulting solution for 5 min at rt. Add 3-(3,4,5-Trimethoxyphenyl)-propionic acid (55 mg, 0.23 mmol) and DMAP (2 mg, 0.02 mmol) and stir the resulting solution for 15 min. Add (2'-Amino-biphenyl-3-yl)-acetic acid methyl ester (49) (50 mg, 0.21 mmol) and stir the reaction solution overnight at rt.

Quench reaction solution with water, separate layers and extract aqu. layer with DCM (3 times). Wash combined organic layer with brine and dry with Na₂SO₄. Purify the crude product by preparative radial chromatography (silica gel, EtOAc/CyH 1+1) to obtain {2'-[3-(3,4,5-Trimethoxy-phenyl)-propionylamino]-biphenyl-3-yl}-acetic acid methyl ester (50) (46 mg, 48%) as a yellow oil. ¹H NMR (400 MHz, CDCl₃): 2.50 (t, 2H, J=7.6 Hz); 2.90 (t, 2H, J=7.7 Hz); 3.64 (s, 2H); 3.65 (s, 3H); 3.77 (s, 6H); 3.78 (s, 3H); 6.38 (s, 2H); 7.09-7.18 (m, 3H); 7.19-7.28 (m, 3H); 7.34 (d, 1H, J=8.1 Hz); 7.38 (d, 1H, J=7.8 Hz); 8.31 (br.d, 1H, J=7.8 Hz).

EXAMPLE 8

4-[3-(3,4,5-Trimethoxy-phenyl)-propionylamino]-benzoic acid methyl ester (52)

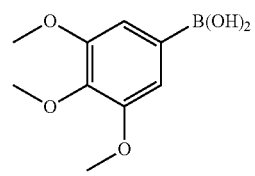

(The following reaction is done in an anhydrous N₂ atmosphere.) Suspend EDC HCl (80 mg, 0.41 mmol) and Et₃N (58 µL, 0.41 mmol) in anhydrous DCM (2.0 mL) and stir the resulting solution for 5 min at rt. Add 3-(3,4,5-Trimethoxy-phenyl)-propionic acid (70 mg, 0.29 mmol) and DMAP (5 mg, 0.04 mmol) and stir the resulting solution for 10 min. Add 4-Amino-benzoic acid methyl ester (51) (42 mg, 0.27 mmol) and stir the reaction solution 2 d at rt. Quench reaction solution with water, separate layers and extract aqu. layer with DCM (3 times). Wash combined organic layer with brine, dry with Na₂SO₄ and filtrate it through a short pad of silica gel using EtOAc to obtain 4-[3-(3,4,5-Trimethoxy-phenyl)-propionylamino]-benzoic acid methyl ester (52) (91 mg, 88%) as a white solid. No further purification. ¹H NMR (400 MHz, CDCl₃): 2.60 (t, 2H, J=7.6 Hz); 2.91 (t, 2H, J=7.6 Hz); 3.70 (s, 6H); 3.76 (s, 3H); 3.83 (s, 3H); 6.35 (s, 2H); 7.55 (d, 2H, J=8.3 Hz); 7.91 (d, 2H, J=8.6 Hz); 8.09 (s, 1H).

EXAMPLE 9

(5-{2-[(3',4',5'-Trimethoxy-biphenyl-2-carbonyl)-amino]-phenyl}-thiophen-2-yl)-acetic acid (59)

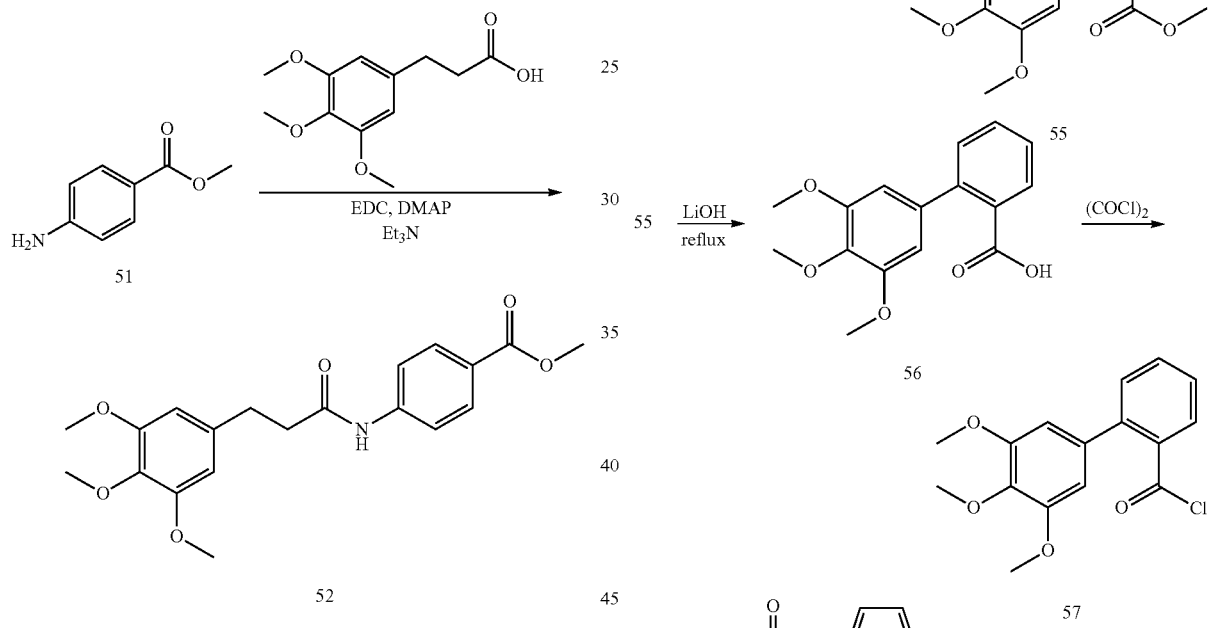

58 —LiOH→

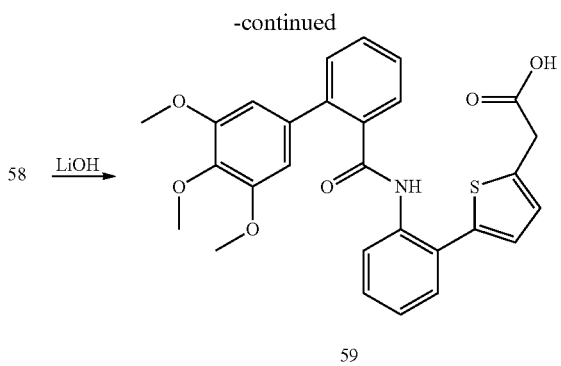

59

Step 1:

(The following reaction is done in an N₂ atmosphere.) To a solution of Methyl-2-bromobenzoate (53) (922 mg, 4.29 mmol) in toluene (11 mL) is added Pd(PPh₃)₄ (297 mg, 0.26 mmol) and Na₂CO₃.10H₂O (3.43 g, 12.00 mmol) in water (3.8 mL). Degas the resulting mixture is carefully (5 times alternating vacuum and flushing with N₂). Add a solution of 3,4,5-Trimethoxyphenylboronic acid (54) (1.00 g, 4.72 mmol) in toluene (10 mL) by syringe, degas the resulting mixture again carefully and stir the resulting mixture overnight at 100° C. Partition the mixture between brine/EtOAc (1+1), separate layers, extract the aqu. layer with EtOAc (3×), wash the combined organic layer with brine and dry with Na₂SO₄. Purify the crude product by flash chromatography (silica gel, EtOAc/CyH 1+7, later 1+5) to obtain 3',4',5'-Trimethoxy-biphenyl-2-carboxylic acid methyl ester (55) as a yellow solid (1.30 g, 99%). ¹H NMR (400 MHz, CDCl₃): 3.65 (s, 3H); 3.84 (s, 6H); 3.87 (s, 3H); 6.52 (s, 2H); 7.35-7.42 (m, 2H); 7.50 (t, 1H, J=8.0 Hz); 7.73 (d, 1H, J=8.0 Hz).

Step 2:

Dissolve 3',4',5'-Trimethoxy-biphenyl-2-carboxylic acid methyl ester (55) (626 mg, 2.08 mmol) in MeOH (14 mL) at rt and add 1M aqu LiOH (4.2 mL, 4.20 mmol). Stir reaction mixture for 8 h under reflux. Remove solvent and partition the residue between 1M aqu. HCl and EtOAc, separate layers, extract the aqu. layer with EtOAc (3×), wash the combined organic layer with brine and dry with Na₂SO₄. Remove solvent and recrystallize residue from EtOAc/CyH 1+2 to obtain 3',4',5'-Trimethoxy-biphenyl-2-carboxylic acid (56) as a white solid (423 mg, 79%). ¹H NMR (400 MHz, CD₃OD: 3.84 (s, 3H); 3.89 (s, 6H); 6.68 (s, 2H); 7.42-7.49 (m, 2H); 7.57 (t, 1H, J=7.5 Hz); 7.76 (d, 1H, J=8.0 Hz).

Step 3:

(The following reaction is done in an anhydrous N₂ atmosphere.) Dissolve 3',4',5'-Trimethoxy-biphenyl-2-carboxylic acid (56) (54 mg, 0.18 mmol) in anhydrous DCM (1.3 mL) and add anhydrous DMF (1 drop, cat. amount). Then add slowly oxalyl chloride (21 µL, 0.24 mmol) by keeping temperature at ca. 20° C. with a water bath and stir the turbid mixture for additional 2 h at it Remove solvent and dry in vacuum to obtain crude 3',4',5'-Trimethoxy-biphenyl-2-carbonyl chloride (57) as a yellow solid. No further purification.

Step 4:

Add a solution of 3',4',5'-Trimethoxy-biphenyl-2-carbonyl chloride (57) (0.18 mmol) in DCM (1.0 mL) to an ice cooled solution of [5-(2-Amino-phenyl)-thiophen-2-yl]-acetic acid methyl ester (36) (46 mg, 0.18 mmol) in anhydrous DCM (2.0 mL) and anhydrous pyridine (0.5 mL). Stir the reaction mixture for 1 h at 0° C. and additional 20 h at rt. Pour the reaction mixture into ice cooled 1M aqu. HCl, extract with EtOAc (2×) and DCM (2×), wash the combined organic layer with brine and dry with Na₂SO₄. Purify the crude product by preparative radial chromatography (silica gel, EtOAc/CyH 1+2) to obtain (5-{2-[(3',4',5'-Trimethoxy-biphenyl-2-carbonyl)-amino]-phenyl}-thiophen-2-yl)-acetic acid methyl ester (58) as a light brown solid (58 mg, 59%). ¹H NMR (400 MHz, CDCl₃): 3.70 (s, 3H); 3.76 (s, 6H); 3.78 (s, 2H); 3.80 (s, 3H); 6.29 (d, 1H, J=3.4 Hz); 6.60 (s, 2H); 6.75 (d, 1H, J=3.4 Hz); 7.07 (t, 1H, J=7.6 Hz); 7.23 (d, 1H, J=7.6 Hz); 7.31 (t, 1H, J=8.0 Hz); 7.37-7.43 (m, 2H); 7.48 (t, 1H, J=7.6 Hz); 7.52 (s, 1H); 7.69 (d, 1H, J=8.0 Hz); 8.45 (d, 1H, J=8.0 Hz).

Step 5:

Dissolve (5-{2-[(3',4',5'-Trimethoxy-biphenyl-2-carbonyl)-amino]-phenyl}-thiophen-2-yl)-acetic acid methyl ester (58) (56 mg, 0.11 mmol) in MeCN (3.8 mL) at rt and add 1M aqu LiOH (760 µL, 0.76 mmol). Stir reaction mixture 18 h at rt. Quench reaction mixture (cooling bath) with 2 M aqu. HCl. Extract the mixture with EtOAc (3×), wash the combined organic layer with brine and dry with Na₂SO₄ to obtain (5-{2-[(3',4',5'-Trimethoxy-biphenyl-2-carbonyl)-amino]-phenyl}-thiophen-2-yl)-acetic acid (59) (55 mg, 99%) as a brown solid. ¹H NMR (400 MHz, CDCl₃): 3.76 (s, 6H), 3.80 (s, 3H); 3.83 (s, 2H); 6.32 (d, 1H, J=3.5 Hz); 6.60 (s, 2H); 6.78 (d, 1H, J=3.5 Hz); 7.07 (t, 1H, J=7.6 Hz); 7.23 (d, 1H, J=7.6 Hz); 7.32 (t, 1H, J=7.6 Hz); 7.36-7.54 (m, 3H); 7.69 (d, 1H, J=8.0 Hz); 8.43 (d, 1H, J=8.0 Hz).

EXAMPLE 10

2',3',4'-Trimethoxy-biphenyl-3-carboxylic acid {2-[5-(1H-tetrazol-5-ylmethyl)-thiophen-2-yl]-phenyl}-amide (87)

SCHEME 17

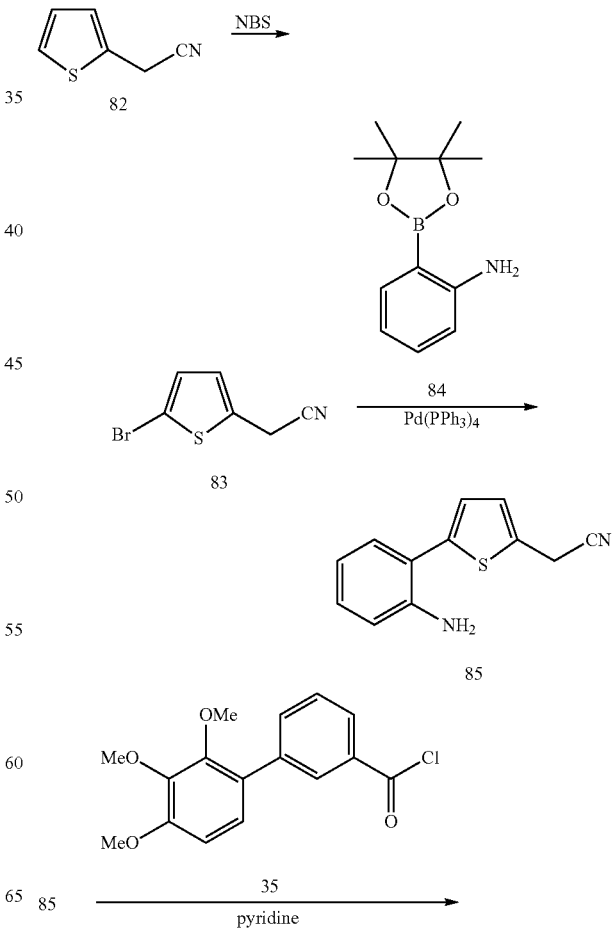

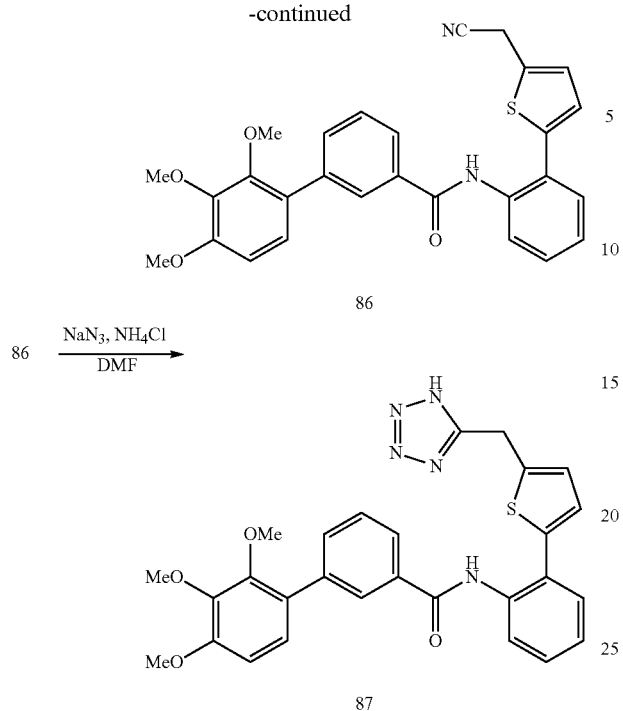

Step 1: (The following reaction is done in an anhydrous N₂ atmosphere.) Dissolve nitrile (82) (500 mg, 4.06 mmol) in anhydrous DMF (2.7 mL), cool to 0° C., add N-bromosuccinimide (795 mg, 7.79 mmol) in portions over a period of 20 min and stir the mixture for 22 h at it Partition the reaction solution between dichloromethane and water (1+1) and extract the separated aqueous layer 2 times with dichloromethane. Wash combined organic layer with water and brine and dry with Na₂SO₄. Remove solvent under reduced pressure and purify the crude product by preparative radial chromatography (silica gel 60PF, CyH/EtOAc 10+1] to obtain (5-bromo-thiophen-2-yl)-acetonitrile (83) as a light yellow liquid (745 mg, 91%). [M. A. Ismail, R. Brun, J. D. Easterbrook, F. A. Tanious, W. D. Wilson, D. W. Boykin, *J. Med Chem.* 2003; 46 (22); 4761-4769]. ¹H NMR (400 MHz, CDCl₃): 3.81 (d, 2H, J=1.0 Hz); 6.81 (d, 1H, $J_1$=3.8 Hz, $J_2$=1.0 Hz); 6.92 (d, 1H, J=3.8 Hz).

Step 2:

(The following reaction is done in an oxygenfree N₂ atmosphere.) Dissolve tetrakis-(triphenylphosphine)-palladium (0) (29 mg, 2.5 mol %) and nitrile (83) (101 mg, 0.50 mmol) in DME (3.7 mL). The reaction mixture is degassed 5 times and flooded with N₂ again. Add 2-(4,4,5,5-tetramethyl-[1,3,2]dioxaborolan-2-yl)phenylamine (84) (120 mg, 0.55 mmol), rinse with DME (0.5 mL), add aqu. 1M NaHCO₃, degas again (5 times) and stir the reaction solution 2 h at 90° C. (reflux). After cooling to rt partition the reaction mixture between EtOAc and brine (1+1) and extract the separated aqueous layer 3 times with EtOAc. Wash combined organic layer with brine and dry with Na₂SO₄. Remove solvent under reduced pressure and purify the crude product by preparative radial chromatography (silica gel 60PF, CyH/EtOAc 2+1) to obtain [5-(2-amino-phenyl)-thiophen-2-yl]-acetonitrile (85) as a brownish oil (84 mg, 78%). ¹H NMR (400 MHz, CDCl₃): 3.89 (br.s, 2H); 5.20-6.50 (br.s, 2H); 6.92 (t, 1H; J=7.6 Hz); 6.95-7.00 (m, 1H); 6.99 (d, 1H; J=3.8 Hz); 7.11 (d, 1H; J=3.8 Hz); 7.21 (dd, 1H; $J_1$=7.6 Hz, $J_2$=1.3 Hz); 7.27 (dd, 1H; $J_1$=7.6 Hz, $J_2$=1.3 Hz).

Step 3:

(The following reaction is done in an anhydrous N₂ atmosphere.) Add a solution of 2',3',4'-trimethoxy-biphenyl-3-carbonyl chloride (35) (117 mg, 0.38 mmol) in dichloromethane (1.3 mL) to an ice cooled solution of the aniline (85) (82 mg, 0.38 mmol) in anhydrous dichloromethane (2.6 mL) and anhydrous pyridine (0.65 mL). Stir the reaction mixture for 1 h at 0° C. and additional 21 h at rt. Pour the reaction mixture into ice cooled 1M aqu. HCl (20 mL), extract with dichloromethane (2×) and EtOAc (1×), wash the combined organic layer with brine and dry with Na₂SO₄. Purify the crude product by preparative radial chromatography (silica gel 60PF, EtOAc/CyH 1+3 (incl. 2% MeOH), later 1+3) to obtain anilide (86) as an orange solid (132 mg, 71%). ¹H NMR (400 MHz, C₆D₆) 2.88 (d, 2H, J=1.0 Hz); 3.53 (s, 3H); 3.55 (s, 3H), 3.94 (s, 3H), 6.63 (d, 1H, J=3.5 Hz); 6.64 (d, 1H, J=8.6 Hz); 6.66 (d, 1H, J=3.5 Hz); 6.99 (td, 1H; $J_1$=7.6 Hz, $J_2$=1.0 Hz); 7.01 (d, 1H, J=8.6 Hz), 7.25-7.34 (m, 3H); 7.74 (dt, 1H; $J_1$=7.8 Hz, $J_2$=1.5 Hz); 7.97 (dt, 1H, $J_1$=7.8 Hz, $J_2$=1.5 Hz), 8.18 (t, 1H, J=1.5 Hz), 8.34 (br. s, 1H); 9.14 (d, 1H, J=7.8 Hz).

Step 4:

(The following reaction is done in an anhydrous N₂ atmosphere.) Dissolve anilide (86) (60 mg, 0.12 mmol) in anhydrous DMF (2.0 mL), add sodium azide (18 mg, 0.14 mmol) and ammonium chloride (9 mg, 0.85 mmol) and stir the reaction solution for 2 d at 90° C. Add again sodium azide (18 mg, 0.14 mmol) and ammonium chloride (9 mg, 0.85 mmol) and stir for additional 3 d at 90° C. Cool mixture to rt and adjust pH=1 by addition of 1M HCl. Extract aqueous layer with dichloromethane (3×). Wash the combined organic layer with brine, dry with Na₂SO₄ and remove solvent under reduced pressure. Purify the crude product by preparative radial chromatography (silica gel, EtOAc/CyH 1+2, later EtOAc/MeOH 9+1) to obtain 2',3',4'-trimethoxy-biphenyl-3-carboxylic acid {2-[5-(1H-tetrazol-5-ylmethyl)-thiophen-2-yl]-phenyl}-amide (87) as a yellow solid (50 mg, 76%) [F. Osterod, L. Peters, A. Kraft, T. Sano, J. J. Morisson, N. Feeder, A. B. Holmes, *J. Mater. Chem.* 2001, 11, 1625-1633 and refer. therein. ¹H-NMR. (400 MHz, (CD₃)₂SO): 3.61 (s, 3H); 3.80 (s, 3H); 3.84 (s, 3H); 4.45 (s, 2H); 6.93 (d, 1H; J=8.6 Hz); 6.93 (d, 1H; J=3.5 Hz); 7.11 (d, 1H, J=8.6 Hz); 7.26 (d, 1H, J=3.5 Hz); 7.33 (td, 1H, $J_1$=7.3 Hz, $J_2$=1.8 Hz); 7.35 (td, 1H, $J_1$=7.3 Hz, $J_2$=1.8 Hz); 7.43-7.47 (m, 1H); 7.53 (t, 1H, J=7.7 Hz); 7.61 (dd, 1H, $J_1$=7.0 Hz, $J_2$=2.0 Hz); 7.66 (d, 1H, J=7.6 Hz); 7.85 (d, 1H, J=7.6 Hz); 7.99 (s, 1H); 10.07 (s, 1H).

EXAMPLE 11

2',3',4'-Trimethoxy-biphenyl-3-carboxylic acid (2-bromo-5-nitro-phenyl)-amide (89)

SCHEME 18

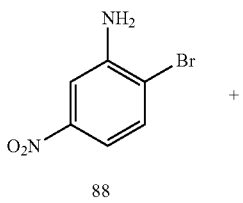

88

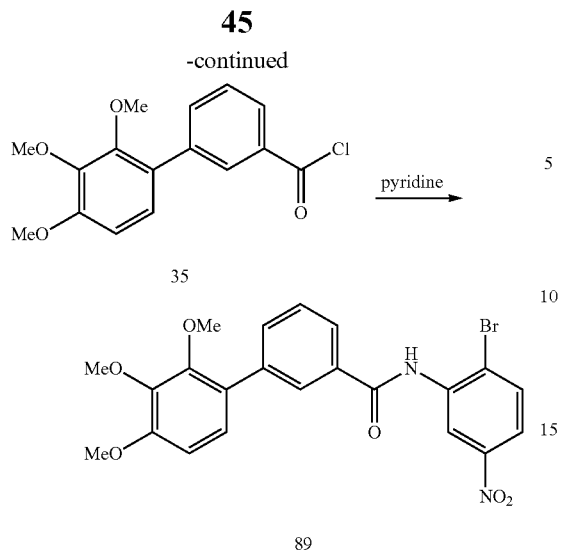

(The following reaction is done in an anhydrous N₂ atmosphere.) Add a solution of 2',3',4'-trimethoxy-biphenyl-3-carbonyl chloride (35) (345 mg, 1.13 mmol) in dichloromethane (5 mL) to an ice cooled solution of 2-bromo-5-nitro-phenylamine (88) (232 mg, 1.07 mmol) in anhydrous dichloromethane (12 mL) and anhydrous pyridine (2.9 mL). Stir the reaction mixture for 15 min at 0° C. and additional 17 h at rt. Pour the reaction mixture into ice cooled 1M aqu. HCl (to get pH ca. 3), extract with EtOAc (3×), wash the combined organic layer with brine and dry it with Na₂SO₄ to afford crude 2',3',4'-trimethoxy-biphenyl-3-carboxylic acid (2-bromo-5-nitro-phenyl)-amide (89) as a beige solid (542 mg, quant.). NMR (400 MHz, CDCl₃): 3.72 (s, 3H); 3.91 (s, 3H); 3.93 (s, 3H); 6.77 (d, 1H, J=8.6 Hz); 7.08 (d, 1H, J=8.6 Hz); 7.56 (t, 1H, J=8.8 Hz); 7.75 (d, 2H, J=8.8 Hz); 7.86 (d, 1H, J=8.8 Hz), 7.87 (d, 1H, J=8.8 Hz); 8.09 (t, 1H, J=1.7 Hz); 8.61 (br. s, 1H); 9.59 (d, 1H, J=2.5 Hz).

EXAMPLE 12

N-(3-Nitro-phenyl)-3-(3,4,5-trimethoxy-phenyl)-propionamide (91)

SCHEME 19

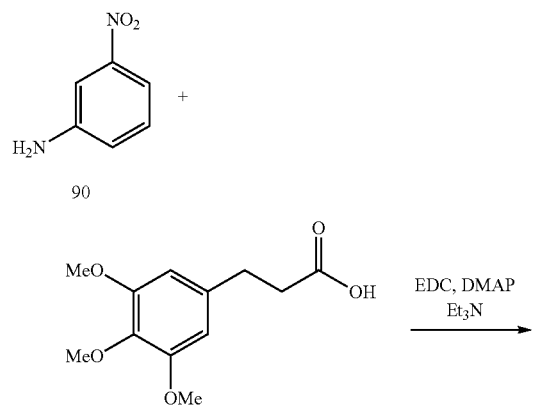

(The following reaction is done in an anhydrous N₂ atmosphere.) Suspend EDC hydrochloride (402 mg, 2.10 mmol) and Et₃N (293 μL, 2.10 mmol) in anhydrous dichloromethane (17.0 mL) and stir the resulting solution for 5 min at rt. Add 3-(3,4,5-trimethoxy-phenyl)-propionic acid (481 mg, 2.00 mmol) and DMAP (24 mg, 0.20 mmol) and stir the resulting solution for 5 min. Add 3-nitro-phenylamine (90) (414 mg, 3.00 mmol) and stir the reaction solution 24 h at rt. Quench reaction solution with sat. aqu. NH₂Cl and water, separate layers and extract aqu. layer with EtOAc (3 times). Wash the combined organic layer with water and brine and dry with Na₂SO₄. Purify the crude product by preparative radial chromatography (silica gel 60PF, EtOAc/CyH 1+1) to obtain N-(3-nitro-phenyl)-3-(3,4,5-trimethoxy-phenyl)-propionamide (91) (508 mg, 70%) as a yellowish solid. ¹H NMR (400 MHz, CDCl₃): 2.65 (t, 2H, J=7.3 Hz); 2.98 (t, 2H, J=7.3 Hz); 3.79 (s, 6H); 3.81 (s, 3H); 6.42 (s, 2H); 7.41 (s, 1H); 7.45 (t, 1H, J=8.0 Hz); 7.84 (d, 1H, J=8.0 Hz); 7.92 (d, 1H, J=8.01 Hz); 8.31 (s, 1H).

The compounds referred to in the following SCHEME 16 are those compounds referred to as the particularly preferred compounds herein.

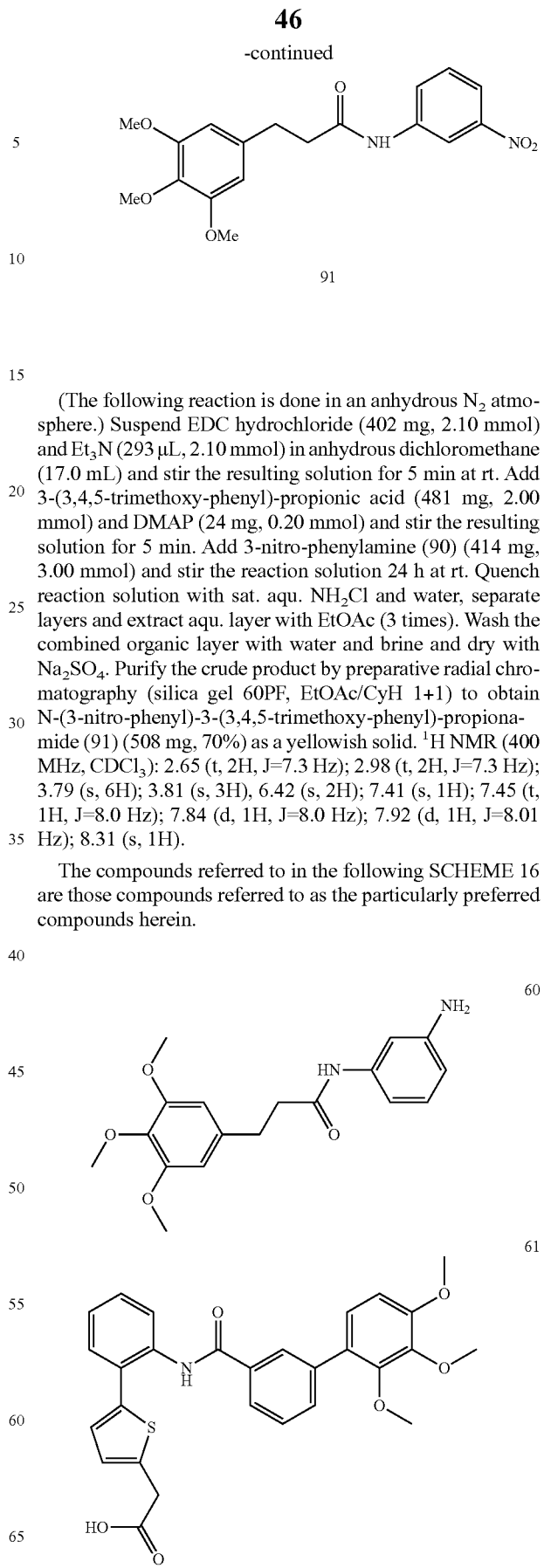

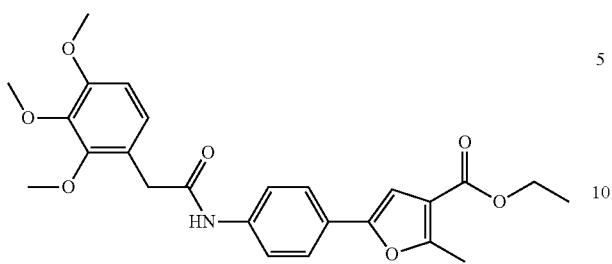
62
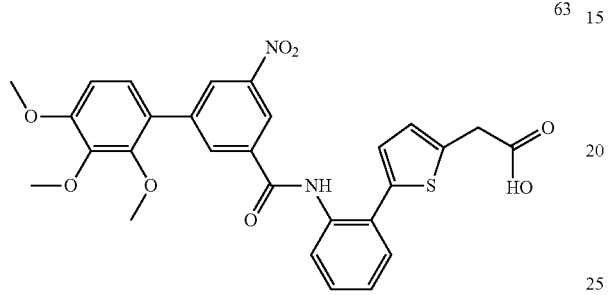
63
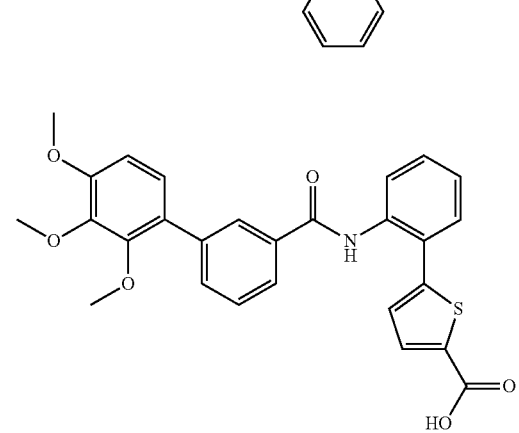
64
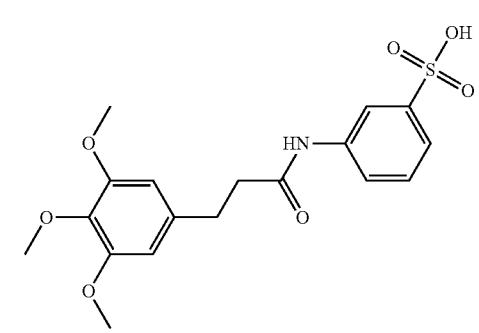
65
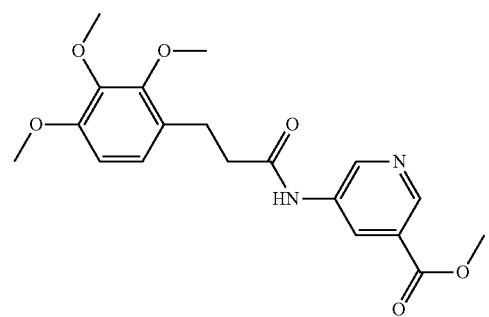
66
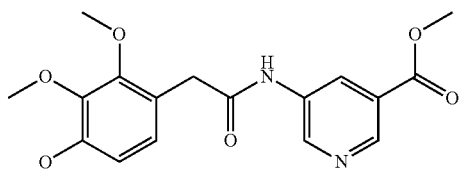
67
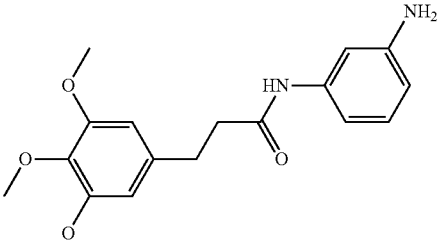
68
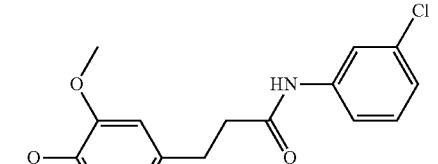
69
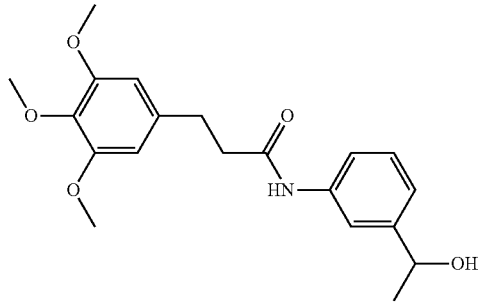
70
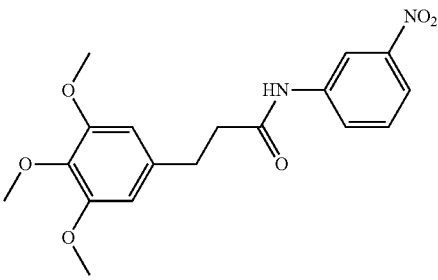
71
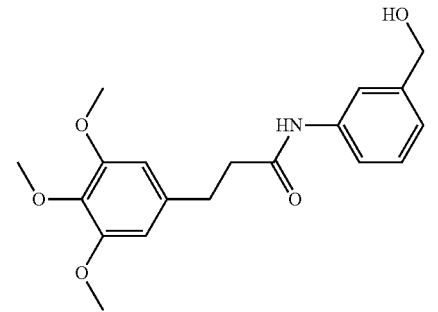
72

73

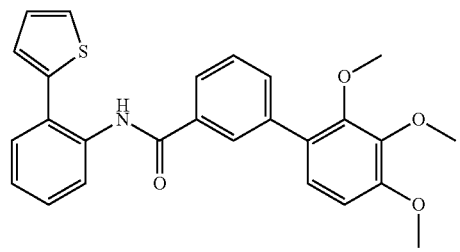

74

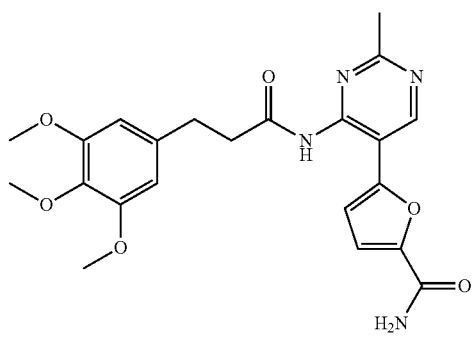

75

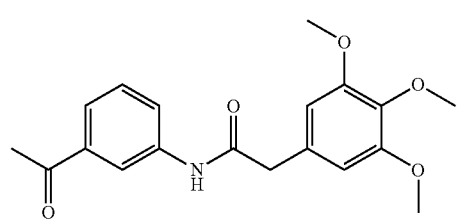

76

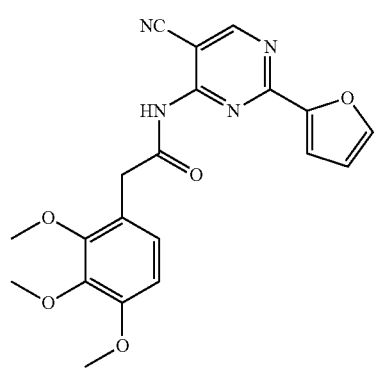

77

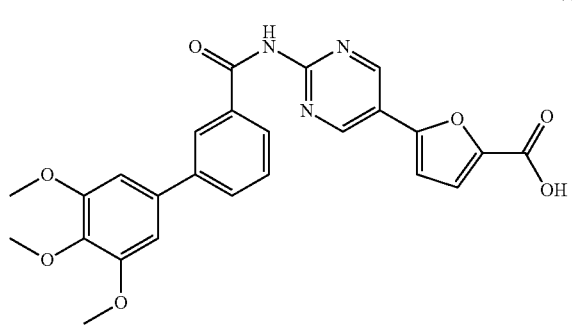

78

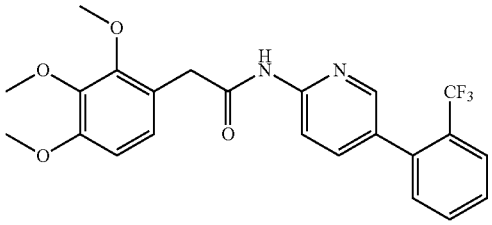

79

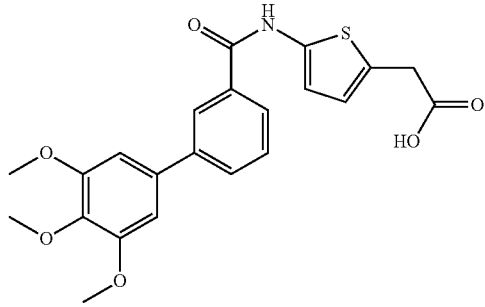

80

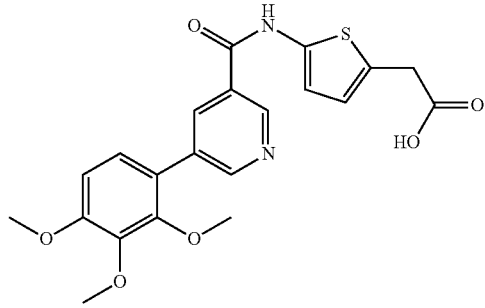

81

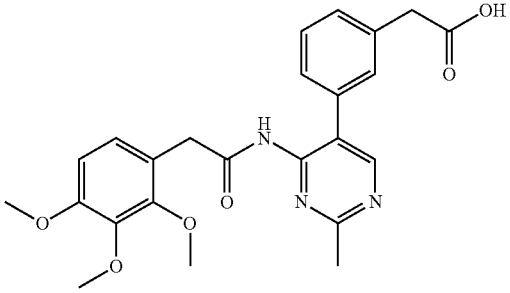

Sialyl Lewis$^x$ Tyrosine Sulfate Assay (sLe$^x$ TSA):

Compounds of the present invention are assayed on a molecular level for their ability to inhibit the binding of P-, L-, or E-selectin chimeric molecules to sLe$^x$ and tyrosinesulfate residues linked to a polymeric matrix as a PSGL-1 substitute. IC$_{50}$-values are determined.

Microtiter plates are coated overnight in carbonate buffer pH9.6 with goat anti human Fc mAB (10 µg/ml). After washing in assay buffer (25 mM 4-(2-hydroxyethyl)-1-piperazineethanesulfonic acid (HEPES), 150 mM NaCl, 1 mM CaCl$_2$, pH7.4) and blocking (3% bovine serum albumin (BSA) in assay buffer) plates are incubated for 2 h at 37° C. with human P-Selectin-IgG-chimera (0.61 nM respectively 150 ng/mL) or human L-Selectin-IgG-chimera (0.61 nM respectively 89 ng/mL) or human E-Selectin-IgG-chimera (0.61 nM respectively 131 ng/mL). 5 µl of sLe$^x$-tyrosine sulfate polyacrylamide (1 mg/ml) carrying 15% sLe$^x$, 10% Tyrosine-sulfate and 5% biotin is complexed with 20 µl Streptavidin-Peroxidase solution (1 mg/ml) and 25 μl assay buffer without CaCl$_2$. For use in the assay, the ligand complex is diluted 1:10000 in assay buffer and further diluted 1:1 with varying amounts of compounds in assay buffer incl. 2% DMSO. This mixture is added to the wells precoated with E- or P-selectin. After incubation for 2 h at 37° C., wells are washed for six times with in assay buffer incl. 0.005% Polyoxyethylenesorbitan monolaurate (TWEEN 20), developed for 10-15 min with 20 μl 3,3',5,5'-tetramethylbenzidine (TMB)/H$_2$O$_2$ substrate solution and stopped with 20 μl 1M H$_2$SO$_4$. Bound sLe$^x$-Tyrosine sulfate ligand complex is determined by measuring optical density at 450 nm vs. 620 nm in a Fusion alpha-FP reader (sold from Packard Bioscience, Dreieich, Germany).

Results from sLe$^x$TSA: IC$_{50}$ Data for E-/P-/L-Selectin

| Compound | IC$_{50}$ E-Selectin [μM] | IC$_{50}$ P-Selectin [μM] | IC$_{50}$ L-Selectin [μM] |
|---|---|---|---|
| Bimosiamose | >500 | 95.0 | >500 |
| 60 | 18.2 | 15.0 | 12.8 |
| 61 | >500 | 186.1 | 385.3 |
| 62 | 74.7 | 46.4 | 45.3 |
| 63 | >500 | 28.5 | 76.1 |
| 64 | >500 | 107.1 | 382.9 |

Results from sLe$^x$TSA: IC$_{50}$ Data for E-/L-Selectin

| Compound | IC$_{50}$ E-Selectin [μM] | IC$_{50}$ P-Selectin [μM] | IC$_{50}$ L-Selectin [μM] |
|---|---|---|---|
| 87 | — | 32.6 | 59.5 |

Flow Chamber Assay/Cell Adhesion and Rolling under Flow Conditions

To assess the capability of compounds to inhibit cell binding under dynamic conditions resembling the flow in a blood vessel, flow chamber assays addressing/testing binding of HL-60 cells/various cell lines to P-selectin, L-selectin and E-selectin chimeric molecules are performed.

Cell attachment under flow conditions are determined using a parallel flow chamber system. A 35 mm polystyrene culture dish is coated for 1 hour at room temperature with coating buffer (50 mM tris-(hydroxymethyl) aminomethane buffer (Tris), 150 mM NaCl, 2 mM CaCl$_2$; pH 7.4) containing human E- or P-selectin-IgG chimera at concentrations of 2.5 μg/ml or 10 μg/ml, respectively. After removal of the coating solution non specific binding sites are blocked for an additional hour with 1% BSA in coating buffer at room temperature. After washing with assay buffer ("Roswell Park Memorial Institute 1640" (RPMI 1640)+10 mM HEPES) the dish is fitted into a parallel plate laminar flow chamber (sold from Glycotech, Rockville, Md.) and mounted on an inverted phase-contrast microscope (sold from Olympus, Hamburg, Germany) equipped with a CCD camera (JVC) that is connected to a PC. Employing a peristaltic pump (sold from Ismatec, Wertheim-Mondfeld, Germany) the re-circulating system is equilibrated with assay buffer containing 125 μM compound or vehicle control (DMSO). Cells (1 million/ml) are added to the chamber and allowed to distribute for 2 minutes at a high flow rate. The flow rate is then decreased resulting in a calculated flow shear of 1 dyne/cm$^2$. Video sequences of 10 low power fields are digitally recorded after 5 minutes continuous flow. The percentage of modulation is calculated from the mean number of cells per field that attached to the coated dish surface in the presence versus absence of compound of at independent experiments.

Data from Flow Chamber Assay for E- and P-Selectin

Values are given as normalized ratios of %-inhibition of compound x divided by %-inhibition of bimosiamose.

| Compound | E-Selectin [Ratio] | P-Selectin [Ratio] |
|---|---|---|
| 63 | 1.46 | 1.06 |
| 64 | 1.27 | 1.01 |
| 87 | 1.23 | 2.62 |

What is claimed is:

1. A compound of the formulas (Ia) or (Ib):

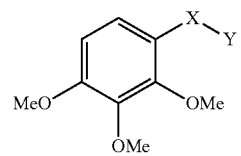

Ia

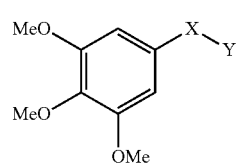

Ib wherein the symbols and substituents have the following meaning:

—X— is

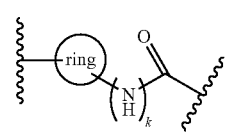

(b)

wherein "ring" is

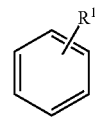

wherein R$^1$ is H, NO$_2$, CF$_3$, F, Cl, Br, I, CN, CH$_3$, NH$_2$, NHAlkyl, NHAryl, NHAcyl, and k=0 or 1;

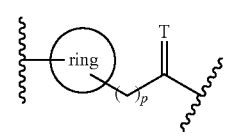

(c)

wherein "ring" is as defined above; T is O, S or [H,H]; p=0, 1, or 2;

—Y is

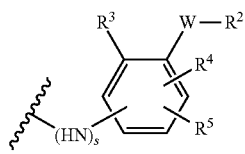

(a)

wherein s is 0 or 1;

R² is CO₂H, CO₂alkyl, CO₂aryl, CO₂NH₂, CO₂aralkyl, CH₂SO₃H, CH₂SO₂NH₂, CH₂PO₂(OH)₂, SO₃H, SO₂NH₂, PO(OH)₂, 1-H-tetrazolyl-, CHO, COCH₃, CH₂OH, CH₂NH₂, NH₂, CH₂NHalkyl, CH₂N(alkyl)alkyl', NHalkyl, N(alkyl)alkyl', OCH₃, CH₂OCH₃, CH₂SH, SH, F, Cl, Br, I, CH₃, CH₂CH₃, CN, or CF₃;

R³ independently from R² is H, CH₃, CH₂CH₃, CF₃, F, Cl, Br, I, CN, or NO₂;

R⁴ independently from R² and R³ is H, CH₃, CH₂CH₃, CF₃, F, Cl, Br, I, CN, NO₂, or R²;

R⁵ is H, NO₂, CF₃, F, Cl, Br, I, CN, CH₃, OCH₃, SH, or NH₂;

—W— is —(CH₂—)ᵥ, cis-CH=CH— or trans-CH=CH—, and v is 0, 1, or 2;

in case that —W— is cis-CH=CH— or trans-CH=CH—, R² must not be NH₂ or SH;

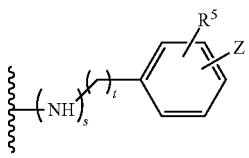

(e)

wherein t is 0, 1, or 2;
—Z is

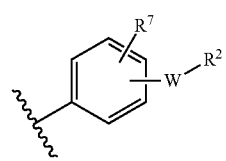

(i)

R⁷ independently from R² is H, NO₂, CF₃, F, Cl, Br, I, CN, CH₃, OCH₃, SH, or NH₂;

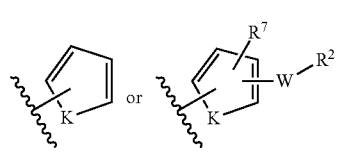

(iv)

in which K is NH, NMe, O, or S;
or a pharmaceutically acceptable salt, ester, or amide thereof of the above identified compounds of formula (Ia) or (Ib).

2. The compound of claim 1 defined by formula (IIa) or (IIb)

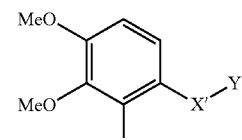

IIa

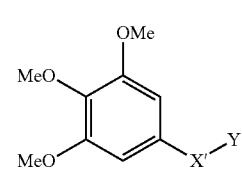

IIb wherein —Y is as defined in claim 1 and —X'— is X(c) as defined in claim 1,
wherein all indices, symbols, and substituents are as defined in claim 1.

3. The compound of claim 1 defined by formulas (A1), (B1), (A2), or (B2):

A1

A2

B1

B2 wherein —X'— is X(c) as defined in claim 1 and —Y is as defined in claim 1 and wherein —X" is

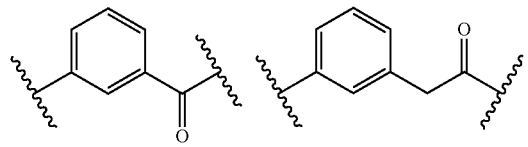 [SMILES: *C(=O)c1cccc(*)c1 ; *C(=O)Cc1cccc(*)c1]

and wherein —Y' is

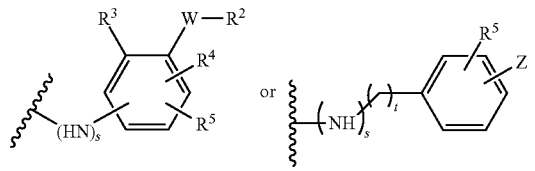

wherein all indices, symbols, and substituents are as defined in claim 1.

4. The compound of claim 1 defined by formulas (C) or (D):

C
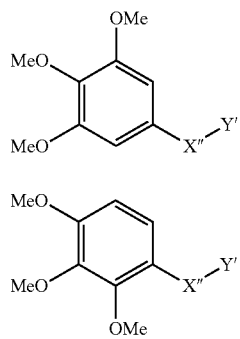

D wherein —X" is

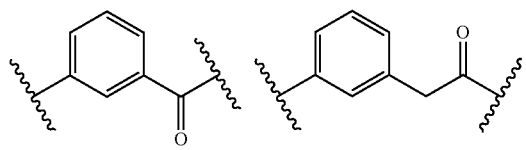 [SMILES: *C(=O)c1cccc(*)c1 ; *C(=O)Cc1cccc(*)c1]

and wherein —Y' is

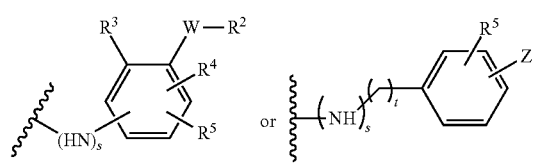

wherein all indices, symbols, and substituents are as defined in claim 1.

5. The compound of claim 1 defined by formulas (E) or (F):

E
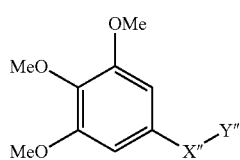

F
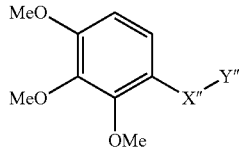

wherein —X" is

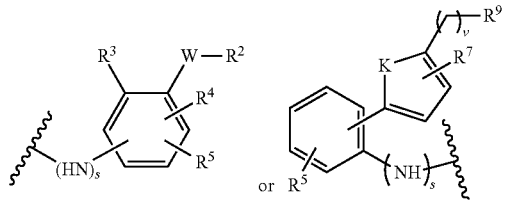

and —Y" is wherein $R^9$ is $CO_2H$, $CO_2alkyl$, $CO_2aryl$, $CO_2NH_2$, $CO_2aralkyl$, $CH_2SO_3H$, $CH_2SO_2NH_2$, $CH_2PO_2(OH)_2$, 1-H-tetrazolyl-, CHO, $COCH_3$, $CH_2OH$, $CH_2NH_2$, $CH_2NHalkyl$, $CH_2N(alkyl)alkyl'$, $CH_2OCH_3$, or $CH_2SH$, wherein all indices, symbols, and substituents are as defined in claim 1.

6. A method of treating Chronic Obstructive Pulmonary Disease (COPD), acute lung injury (ALI), cardiopulmonary bypass, acute respiratory distress syndrome (ARDS), Crohn's disease, septic shock, sepsis, chronic inflammatory diseases such as psoriasis, atopic dermatitis, and rheumatoid arthritis, and reperfusion injury that occurs following heart attacks, strokes, atherosclerosis, and organ transplants, traumatic shock, multi-organ failure, autoimmune diseases like multiple sclerosis, percutaneous transluminal angioplasty, asthma and inflammatory bowel disease, comprising the administration of a therapeutic amount of at least one compound of claim 1.

7. A method of treating Chronic Obstructive Pulmonary Disease (COPD), acute lung injury (ALI), cardiopulmonary bypass, acute respiratory distress syndrome (ARDS), Crohn's disease, septic shock, sepsis, chronic inflammatory diseases such as psoriasis, atopic dermatitis, and rheumatoid arthritis, and reperfusion injury that occurs following heart attacks, strokes, atherosclerosis, and organ transplants, traumatic shock, multi-organ failure, autoimmune diseases like multiple sclerosis, percutaneous transluminal angioplasty, asthma and inflammatory bowel disease, comprising the administration of a therapeutic amount of at least one compound of claim 4.

8. A method of treating or diagnosing inflammatory disorders, comprising the administration of a therapeutic amount of at least one compound of claim 1.

9. A cosmetic or dermatological composition, comprising at least one compound of claim 1.

10. A cosmetic composition comprising at least one compound of claim 1 and at least one cosmetically tolerable component.

11. A dermatological composition comprising at least one compound of claim 1 and at least one dermatologically tolerable component.

12. A pharmaceutical composition comprising at least one compound of claim 1 and a pharmaceutically acceptable excipient.

13. A pharmaceutical composition comprising at least one compound of claim 2 and a pharmaceutically acceptable excipient.

14. A pharmaceutical composition comprising at least one compound of claim 3 and a pharmaceutically acceptable excipient.

15. A pharmaceutical composition comprising at least one compound of claim 4 and a pharmaceutically acceptable excipient.

16. A pharmaceutical composition comprising at least one compound of claim 5 and a pharmaceutically acceptable excipient.

* * * * *